US008044187B2

(12) United States Patent
Szkudlinski et al.

(10) Patent No.: US 8,044,187 B2
(45) Date of Patent: *Oct. 25, 2011

(54) HUMAN LUTEINIZING HORMONE SUPERAGONISTS

(75) Inventors: Mariusz W. Szkudlinski, Potomac, MD (US); Bruce D. Weintraub, North Potomac, MD (US); Mathis Grossmann, Parkville (AU)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 25 days.

This patent is subject to a terminal disclaimer.

(21) Appl. No.: 12/467,081

(22) Filed: May 15, 2009

(65) Prior Publication Data

US 2009/0233846 A1    Sep. 17, 2009

Related U.S. Application Data

(60) Division of application No. 11/409,428, filed on Apr. 21, 2006, now Pat. No. 7,687,610, which is a continuation of application No. 10/057,113, filed on Jan. 25, 2002, now Pat. No. 7,070,788, which is a division of application No. 09/185,408, filed on Nov. 3, 1998, now Pat. No. 6,361,992, which is a continuation of application No. PCT/US96/06483, filed on May 8, 1996.

(51) Int. Cl.
*C07K 14/59* (2006.01)

(52) U.S. Cl. .................... 536/23.51; 435/69.4; 435/325; 435/252.3; 435/320.1; 424/198.1; 530/398

(58) Field of Classification Search .................... None
See application file for complete search history.

(56) References Cited

U.S. PATENT DOCUMENTS

| | | | |
|---|---|---|---|
| 5,503,995 | A | 4/1996 | Khudyakov et al. |
| 6,361,992 | B1 | 3/2002 | Szkudlinski et al. |

FOREIGN PATENT DOCUMENTS

| | | |
|---|---|---|
| EP | 0 404 458 A2 | 6/1990 |
| EP | 1 947 117 A3 | 10/2008 |
| JP | 55-500899 | 11/1980 |
| JP | 61-76421 | 4/1986 |
| JP | 64-45317 | 2/1989 |
| WO | WO 90/02812 | 3/1990 |
| WO | WO 91/16922 | 11/1991 |

OTHER PUBLICATIONS

Abrahmsen, L., et al., Engineering Subtilisin and Its Substrates for Efficient Ligation of Peptide Bonds in Aqueous Solution. Biochemistry, 30:4151 (1991).
Ascoli, M., Characterization of Several Clonal Lines of Cultured Leydig Tumor Cells: Gonadotropin Receptors and Steroidgenic Responses. Endocrinology, 108:88-95 (1981).
Baggiolini, M. and Clark-Lewis, et al., Interleukin-8, a chemotactic and inflammatory cytokine. FEBS Letter, 307(1):97-101 (Jul. 1992).
Ben-Rafael, Z., et al., Pharmacokinetics of follicle-stimulating hormone: clinical significance. Fertility and Sterility, 63(4):689-700 (1995).
Benua, R. S., et al., An 18 Year Study of the Use of Beef Thyrotropin to Increase $I^{131}$ Uptake in Metastatic Thyroid Cancer. J. Nucl. Med., 5:796-801 (1964).
Bodansky and Trost, Eds., "Principles of Peptide Synthesis", Springer-Verlag, Inc., N.Y. (1993) (Title page only).
Brake, A. J., et al., α-Factor-directed synthesis and secretion of mature foreign proteins in *Saccharomyces cerevisiae*. Proc. Natl. Acad. Sci. USA, 81:4642-4646 (1984).
Campbell, R. K., et al., Conversion of human choriogonadotropin into a follitropin by protein engineering. Proc. Natl. Acad. Sci. USA, 88:760-764 (1991).
Clark-Lewis, I., et al., Chemical Synthesis, Purification, and Characterization of Two Inflammatory Proteins, Neutrophil Activating Peptide 1 (Interleukin-8) and Neutrophil Activating Peptide 2. Biochemistry. 30:3128-3135 (1991).
Clark-Lewis, I., et al., Structural Requirements for Interleukin-8 Function Identified by Design of Analogs and CXC Chemokine Hybrids. J. Biol. Chem., 269(23):16075-16081 (1994).
Clore, G. M., et al., Three-Dimensional Structure of Interleukin 8 in Solution. Biochemistry, 29:1689-1696 (1990).
Combarnous, Y., Molecular Basis of the Specificity of Binding of Glycoprotein Hormones to Their Receptors. Endocrine Rev., 13(4):670-691 (1992). Cunningham, B. C., et al., Receptor and Antibody Epitopes in Human Growth Hormone Identified by Homolog-Scanning Mutagenesis. Science 243:1330-1336 (1989).
Dawson, P. E., et al. Synthesis of Proteins by Native Chemical Ligation. Science, 266:776-779 (1994).
De Lisle Milton, R. C., et al., Synthesis of Proteins by Chemical Ligation of Unprotected Peptide Segments: Mirror-Image Enzyme Molecules, D- & L-HIV Protease Analogs. "Techniques in Protein Chemistry IV," Academic Press, New York, pp. 257-267 (1993).

(Continued)

*Primary Examiner* — Lorraine Spector
(74) *Attorney, Agent, or Firm* — Swanson & Bratschun, L.L.C.

(57) ABSTRACT

The invention is directed toward a human glycoprotein hormone having at least one, two, three, four, or five basic amino acids in the α-subunit at positions selected from the group consisting of positions 11, 13, 14, 16, 17, and 20. The invention is also directed to a human glycoprotein where at least one of the amino acids at position 58, 63, and 69 of the β-subunit of the human thyroid stimulating hormone are basic amino acids. The invention is further directed to a modified human glycoprotein hormone having increased activity over a wild-type human glycoprotein hormone, where the modified human glycoprotein comprises a basic amino acid substituted at a position corresponding to the same amino acid position in a non-human glycoprotein hormone having an increased activity over the wild-type human glycoprotein hormone. The invention is also directed to a method of constructing superactive nonchimeric analogs of human hormones comprising comparing the amino acid sequence of a more active homolog from another species to the human hormone, and selecting superactive analogs from the substituted human hormones. The invention is also directed to nucleic acids encoding the modified human glycoprotein hormones, vectors containing those nucleic acids, and host cells containing those vectors.

42 Claims, 15 Drawing Sheets

OTHER PUBLICATIONS

Dias, J. A., et al., Receptor Binding and Functional Properties of Chimeric Human Follitropin Prepared by an Exchange between a Small Hydrophilic Intercysteine Loop of Human Follitropin and Human Lutropin. J. Biol. Chem., 269(41):25289-25294 (1994).

Dirnhofer, S., et al., Free α subunit of human chorionic gonadotrophin: molecular basis of immunologically and biologically active domains. J. Endocrinol., 140:145-154 (1994).

Ferretti, L., et al, Total synthesis of a gene for bovine rhodopsin. Proc. Natl. Acad. Sci. USA, 83:599-603 (1986).

Fiddes, J. C., et al., Isolation, cloning and sequence analysis of the cDNA for the α-subunit of human chorionic gonadotropin. Nature, 281:351-356 (1979).

Fiddes J. C. and Goodman H. M. 1980 "The cDNA for the b-subunit of human chorionic gonadotropin suggests evolution of a gene by readthrough into the 3' untranslated region" Nature 286:684-687.

Fontaine, Y.-A. and Burzawa-Gerard, E., Esquisse de l'Evolution des Hormones Gonadotropes et Thyreotropes des Vertebres. Gen. Comp. Endocrinol., 32:341-347 (1977).

Golos, T. G., et al., Molecular Cloning of the Rhesus Glycoprotein Hormone α-Subunit Gene. DNA and Cell Biol., 10(5):367-380 (1991).

Grant, G. A., "Synthetic Peptides: A User Guide". W.H. Freeman and Co., N,Y. (1992) (Title page only).

Grossmann, M., et al., Role of the Carboxy-Terminal Residues of the α-Subunit in the Expression and Bioactivity of Human Thyroid-Stimulating Hormone. Mol. Endocrinol. 9(8):948-958 (1995).

Hershman, J. M. and Edwards, C. L., Serum Thyrotropin (TSH) Levels after Thyroid Ablation Compared with TSH Levels after Exogenous Bovine TSH: Implications for $^{131}$I Treatment of Thyroid Carcinoma. J. Clin. Endocrinol. Metab., 34:814-818 (1972).

Hayashizaki, Y. et al. 1985 "Molecular cloning of the human thyrotropin-b subunit gene" FEBS Letters 188:394-400.

Igarashi, S., et al., Functional expression of recombinant human luteinizing hormone. Biochem. Biophys. Res. Commun., 201(1):248-256 (1994).

Ji, I., et al., Receptor Activation of and Signal Generation by the Lutropin/Choriogonadotropin Receptor. Biol. Chem., 268(31):22971-22974 (1993).

Jiang, X., et al., Structural predictions for the ligand-binding region of glycoprotein hormone receptors and the nature of hormone-receptor interactions. Structure, 3:1341-1353 (1995).

Joshi, L., et al., Recombinant Thyrotropin Containing a β-Subunit Chimera with the Human Chorionic Gonadotropin-β Carboxy-Terminus Is Biologically Active, with a Prolonged Plasma Half-Life: Role of Carbohydrate in Bioactivity and Metabolic Clearance. Endocrinology, 136(9):3839-3848 (1995).

Kajava, A. V., et al., Modeling of the three-dimensional structure of proteins with the typical leucine-rich repeats. Structure, 3:867-877 (1995).

Kato JY et al. 1986 "Amino acid substitutions sufficient to convert the nontransforming p60c-src protein to a transforming protein." Mol Cell Biol 6:4155-4160.

Keene J. L. et al. 1989 "Expression of biologically active human follitropin in Chinese Hamster Ovary cells" J Biol Chem 264:4769-4775.

Kim DH et al. 1996 "Characterization of a Cys115 to Asp substitution in the Escherichia coli cell wall biosynthetic enzyme UDP-GlcNAc enolpyruvyl transferase (MurA) that confers resistance to inactivation by the antibiotic fosfomycin." Biochemistry 35:4923-4928.

Lapthorn, A. J., et al., Crystal structure of human chorionic gonadotropin. Nature, 369:455-461 (1994).

Leinung, M. C., et al., Synthetic Analogs of the Carboxyl-Terminus of β-Thyrotropin: The Importance of Basic Amino Acids in Receptor Binding Activity. Biochemistry, 31(41):10094-10098 (1992).

Licht, P., et al., Evolution of Gonadotropin Structure and Function. Rec. Progr. Horm. Res. 50:169-248 (1997).

Liu, C., et al., Site-directed Alanine Mutagenesis of Phe$^{33}$, Arg$^{35}$, and Arg$^{42}$-Ser$^{43}$-Lys$^{44}$ in the Human Gonadotropin α-Subunit. J. Biol. Chem., 268(29):21613-21617 (1993).

Liu, W-K., et al., The Role of the Amino Group in Subunit Association and Receptor Site Interaction for Ovine Luteinizing Hormone as Studied by Acylation. J. Biol., Chem., 249(17):5544-5550 (1974).

Lunardi-Iskandar, Y., et al., Tumorigenesis and metastasis of neoplastic Kaposi's sarcoma cell line in immunodeficient mice blocked by a human pregnancy hormone. Nature, 375:64-68 (1995).

Meier, C. A., et al., Diagnostic Use of Recombinant Human Thyrotropin in Patients with Thyroid Carcinoma (Phase I/II Study). J. Clin. Endocrinol. Metab., 78:188-196 (1994).

Moyle, W. R., et al., Model of Human Chorionic Gonadotropin and Lutropin Receptor Interaction That Explains Signal Transduction of the Glycoprotein Hormones. J. Biol. Chem., 270(34):20020-20031 (1995).

Moyle, W. R., Co-evolution of ligand-receptor pairs. Nature, 368:251-255 (1994).

Pierce, J. G. and Parsons, T. F., Glycoprotein Hormones: Structure and Function. Ann. Rev. Biochem., 50:465-495 (1981).

Remington's Pharmaceutical Sciences, Eighteenth Edition (Mack Publishing Co., Easton, PA) (1990) (Title page only).

Sambrook, J., et al., "Molecular Cloning, a Laboratory Manual," Cold Spring Harbor Laboratory Press (1989) (Title page only).

Sarkar, G. and Sommer, S. S., The "Megaprimer" Method of Site-Directed Mutagenesis. BioTechniques, 8(4):404-407 (1990).

Schnolzer, M. and Kent, S. B. H., Constructing Proteins by Dovetailing Unprotected Synthetic Peptides: Backbone-Engineered HIV Protease. Science, 256:221-225 (1992).

Smith, M., In Vitro Mutagenesis. Ann. Rev. Genet., 19:423-462 (1985).

Stanton, P. G. and Hearn, M. T. W., The Iodination Sites of Bovine Thyrotropin. J. Biol. Chem., 262(4):1623-1632 (1987).

Szkudlinski, M. W., et al., Purification and Characterization of Recombinant Human Thyrotropin (TSH) Isoforms Produced by Chinese Hamster Ovary Cells: The Role of Sialylation and Sulfation in TSH Bioactivity. Endocrinology, 133(4):1490-1503 (1993).

Szkudlinski, M. W., et al., Subunit-specific functions of N-linked oligosaccharides in human thyrotropin: Role of terminal residues of α- and β-subunit oligosaccharides in metabolic clearance and bioactivity. Proc. Natl. Acad. Sci. USA, 92: 9062-9066 (1995).

Talmadge K et al. 1984 "Evolution of the genes for the b subunits of human chorionic gonadotropin and luteinizing hormone" Nature 307:37-40.

Theill, L. E. and Karin, M., "Transcriptional control of GH expression and anterior pituitary development" Endocrine Reviews 14(6):670-689 (1993).

Ward, D. N., et al., Chemical Reduction-Reoxidation of the Glycoprotein Hormone Disulfide Bonds. Ballet and Bidard (eds) "Structure-function relationships of gonadotropins," Serono Symposium Publications, Raven Press, New York, 65:1-19 (1990).

Wilson, J. M., et al., Superovulation of cattle with a recombinant-DNA bovine follicle stimulating hormone. Animal Reproductive Science, 33:71-82 (1993).

Wu, H., et al., Structure of human chorionic gonadotropin at 2.6 Å resolution from MAD analysis of the selenomethionyl protein. Structure, 2:545-558 (1994).

Yadav, S. P., et al., Holoprotein Formation of Human Chorionic Gonadotropin: Differential Trace Labeling with Acetic Anhydride. Mol. Endocrinol., 8:1547-1558 (1994).

Yamazaki, K., et al., Potent Thyrotropic Activity of Human Chorionic Gonadotropin Variants in Terms of $^{125}$I Incorporation and de Novo Synthesized Thyroid Hormone Release in Human Thyroid Follicles. J. Clin. Endocrinol. Metab., 80(2):473-479 (1995).

Zoller, M. J., New molecular biology methods for protein engineering. Curr. Opin. Struct. Biotechnol., 2:526-531 (1991).

Canadian Intellectual Property Office Communication dated Dec. 21, 2006 pursuant to Canadian Application 2,253,441.

Japanese Patent Office Communication dated Sep. 11, 2007, pursuant to Japanese Patent Application No. 2007-124785.

Partial European Search Report dated Jun. 12, 2008, pursuant to European Patent Application No. EP 07 15 0018.

Canadian Intellectual Property Office Communication dated Mar. 10, 2009, pursuant to Canadian Patent Application No. 2,253,441.

| | 10 | 11 | 12 | 13 | 14 | 15 | 16 | 17 | 18 | 19 | 20 | 21 | SEQ. I.D. No. |
|---|---|---|---|---|---|---|---|---|---|---|---|---|---|
| Human | Cys | Thr | Leu | Gln | Glu | Asn | Pro | Phe | Phe | Ser | Gln | Pro | 3 |
| Chimpanzee | — | — | — | — | — | — | — | — | — | — | — | — | 4 |
| Orangutan | — | — | — | — | — | — | — | — | — | — | — | — | 5 |
| Gibbon | — | Gln | — | His | — | — | Gln | — | — | — | — | — | 6 |
| Baboon | — | Lys | Pro | Arg | — | — | Lys | — | — | — | Lys | — | 7 |
| Rhesus | — | Lys | Pro | Arg | — | — | Lys | — | — | — | Lys | — | 8 |
| Marmoset | — | Lys | — | Lys | — | — | Lys | — | — | — | Arg | Leu | 9 |
| Bovine | — | Lys | — | Lys | — | — | Lys | Tyr | — | — | Lys | — | 10 |
| Ovine | — | Lys | — | Arg | — | — | Lys | Tyr | — | — | Lys | — | 11 |
| Equine | — | Lys | — | Arg | — | — | Lys | Tyr | — | Phe | Lys | Leu | 12 |
| Porcine | — | Lys | — | Lys | — | — | Lys | Tyr | — | — | Lys | Leu | 13 |
| Rabbit | — | Lys | — | Lys | — | — | Lys | Tyr | — | — | Lys | Leu | 14 |
| Mouse | — | Lys | — | Lys | — | — | Lys | Tyr | — | — | Lys | Leu | 15 |
| Rat | — | Lys | — | Lys | — | — | Lys | Tyr | — | — | Lys | Leu | 16 |
| Whale | — | Lys | — | Lys | Gln | — | Lys | — | — | — | — | — | 17 |
| Quail | — | Lys | — | Gly | — | — | Arg | — | — | — | Lys | — | 18 |
| Chicken | — | Lys | — | Gly | — | — | Arg | — | — | — | Lys | — | 19 |
| Turkey | — | Lys | — | Gly | — | — | Arg | — | — | — | Lys | — | 20 |
| Bullfrog | — | Arg | — | Lys | — | — | Leu | Arg | — | — | Asn | Met | 21 |
| Salmon 1 | — | Lys | — | Lys | — | — | Lys | Val | — | — | Asn | — | 22 |
| Salmon 2 | — | — | — | Lys | Pro | — | Thr | Ile | — | Pro | Asn | — | 23 |
| Catfish | — | Lys | — | Lys | — | — | Asn | Ile | — | — | Lys | — | 24 |
| Tuna | — | — | — | Lys | Lys | — | Asn | Val | — | — | Arg | Asp | 25 |
| Yellowfin | — | — | — | Arg | Lys | — | Thr | Val | — | — | Arg | Asp | 26 |
| Bass | — | — | — | Arg | Lys | — | Ser | Val | — | — | Arg | Asp | 27 |
| Carp 1 | — | Lys | — | Lys | — | — | Asn | Ile | — | — | Lys | — | 28 |
| Carp 2 | — | — | — | Lys | — | — | Asn | Ile | — | — | Lys | — | 29 |
| Pike eel | — | Arg | — | Lys | Asp | — | Lys | — | — | — | Lys | — | 30 |
| Eel | — | Arg | — | — | — | — | Lys | Ile | — | — | Lys | — | 31 |

*FIG. 1A*

| | 10 Cys | 11 Thr | 12 Leu | 13 Gln | 14 Glu | 15 Asn | 16 Pro | 17 Phe | 18 Phe | 19 Ser | 20 Gln | 21 Pro | SEQ. I.D. No. |
|---|---|---|---|---|---|---|---|---|---|---|---|---|---|
| Human | Cys | Thr | Leu | Gln | Glu | Asn | Pro | Phe | Phe | Ser | Gln | Pro | 3 |
| Q13K | — | — | — | Lys | — | — | — | — | — | — | — | — | 32 |
| P16K | — | — | — | — | — | — | Lys | — | — | — | — | — | 33 |
| Q20K | — | — | — | — | — | — | — | — | — | — | Lys | — | 34 |
| P16K+Q20K | — | — | — | — | — | — | Lys | — | — | — | Lys | — | 35 |
| P16K+Q20K+Q13K | — | — | — | Lys | — | — | Lys | — | — | — | Lys | — | 36 |
| P16K+Q20K+Q13K+E14K | — | — | — | Lys | Lys | — | Lys | — | — | — | Lys | — | 37 |

SEQUENCE LISTING

<160> NUMBER OF SEQ ID NOS: 37

<210> SEQ ID NO 1
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 1
cctgatagat tgcccagaat gc                                              22

<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 2
gtgataataa caagtactgc agtg                                            24

<210> SEQ ID NO 3
<211> LENGTH: 12
<212> TYPE: PRT
<213> ORGANISM: Homo sapiens

<400> SEQUENCE: 3

Cys Thr Leu Gln Glu Asn Pro Phe Phe Ser Gln Pro
 1               5                  10

<210> SEQ ID NO 4
<211> LENGTH: 12
<212> TYPE: PRT
<213> ORGANISM: Pan troglodytes

<400> SEQUENCE: 4

Cys Thr Leu Gln Glu Asn Pro Phe Phe Ser Gln Pro
 1               5                  10

<210> SEQ ID NO 5
<211> LENGTH: 12
<212> TYPE: PRT
<213> ORGANISM: Pongo pygmaeus

<400> SEQUENCE: 5

Cys Thr Leu Gln Glu Asn Pro Phe Phe Ser Gln Pro
 1               5                  10

<210> SEQ ID NO 6
<211> LENGTH: 12
<212> TYPE: PRT
<213> ORGANISM: Hylobates sp.

<400> SEQUENCE: 6

Cys Gln Leu His Glu Asn Pro Phe Phe Ser Gln Pro
 1               5                  10

<210> SEQ ID NO 7
<211> LENGTH: 12
<212> TYPE: PRT
<213> ORGANISM: Papio anubis

<400> SEQUENCE: 7

-continued

Cys Lys Pro Arg Glu Asn Gln Phe Phe Ser Lys Pro
 1               5                  10

<210> SEQ ID NO 8
<211> LENGTH: 12
<212> TYPE: PRT
<213> ORGANISM: Macaca mulatta

<400> SEQUENCE: 8

Cys Lys Pro Arg Glu Asn Lys Phe Phe Ser Lys Pro
 1               5                  10

<210> SEQ ID NO 9
<211> LENGTH: 12
<212> TYPE: PRT
<213> ORGANISM: Callithrix jacchus

<400> SEQUENCE: 9

Cys Lys Leu Lys Glu Asn Lys Tyr Phe Ser Arg Leu
 1               5                  10

<210> SEQ ID NO 10
<211> LENGTH: 12
<212> TYPE: PRT
<213> ORGANISM: Bos taurus

<400> SEQUENCE: 10

Cys Lys Leu Lys Glu Asn Lys Tyr Phe Ser Lys Pro
 1               5                  10

<210> SEQ ID NO 11
<211> LENGTH: 12
<212> TYPE: PRT
<213> ORGANISM: Ovis aries

<400> SEQUENCE: 11

Cys Lys Leu Lys Glu Asn Lys Tyr Phe Ser Lys Pro
 1               5                  10

<210> SEQ ID NO 12
<211> LENGTH: 12
<212> TYPE: PRT
<213> ORGANISM: Equus caballus

<400> SEQUENCE: 12

Cys Lys Leu Arg Glu Asn Lys Tyr Phe Phe Lys Leu
 1               5                  10

<210> SEQ ID NO 13
<211> LENGTH: 12
<212> TYPE: PRT
<213> ORGANISM: Sus scrofa

<400> SEQUENCE: 13

Cys Lys Leu Lys Glu Asn Lys Tyr Phe Ser Lys Leu
 1               5                  10

<210> SEQ ID NO 14
<211> LENGTH: 12
<212> TYPE: PRT
<213> ORGANISM: Oryctolagus cuniculus

<400> SEQUENCE: 14

Cys Lys Leu Lys Glu Asn Lys Tyr Phe Ser Lys Leu
 1               5                  10

```
<210> SEQ ID NO 15
<211> LENGTH: 12
<212> TYPE: PRT
<213> ORGANISM: Mus musculus

<400> SEQUENCE: 15

Cys Lys Leu Lys Glu Asn Lys Tyr Phe Ser Lys Leu
1               5                   10

<210> SEQ ID NO 16
<211> LENGTH: 12
<212> TYPE: PRT
<213> ORGANISM: Rattus norvegicus

<400> SEQUENCE: 16

Cys Lys Leu Lys Glu Asn Lys Tyr Phe Ser Lys Leu
1               5                   10

<210> SEQ ID NO 17
<211> LENGTH: 12
<212> TYPE: PRT
<213> ORGANISM: Balaenoptera sp.

<400> SEQUENCE: 17

Cys Lys Leu Lys Gln Asn Lys Tyr Phe Ser Lys Leu
1               5                   10

<210> SEQ ID NO 18
<211> LENGTH: 12
<212> TYPE: PRT
<213> ORGANISM: Coturnix coturnix

<400> SEQUENCE: 18

Cys Lys Leu Gly Glu Asn Arg Phe Phe Ser Lys Pro
1               5                   10

<210> SEQ ID NO 19
<211> LENGTH: 12
<212> TYPE: PRT
<213> ORGANISM: Gallus gallus

<400> SEQUENCE: 19

Cys Lys Leu Gly Glu Asn Arg Phe Phe Ser Lys Pro
1               5                   10

<210> SEQ ID NO 20
<211> LENGTH: 12
<212> TYPE: PRT
<213> ORGANISM: Meleagris gallopavo

<400> SEQUENCE: 20

Cys Lys Leu Gly Glu Asn Arg Phe Phe Ser Lys Pro
1               5                   10

<210> SEQ ID NO 21
<211> LENGTH: 12
<212> TYPE: PRT
<213> ORGANISM: Rana catesbeiana

<400> SEQUENCE: 21

Cys Arg Leu Lys Glu Asn Leu Arg Phe Ser Asn Met
1               5                   10

<210> SEQ ID NO 22
<211> LENGTH: 12
```

```
<212> TYPE: PRT
<213> ORGANISM: Salmo salar

<400> SEQUENCE: 22

Cys Lys Leu Lys Glu Asn Lys Val Phe Ser Asn Pro
 1               5                  10

<210> SEQ ID NO 23
<211> LENGTH: 12
<212> TYPE: PRT
<213> ORGANISM: Salmo salar

<400> SEQUENCE: 23

Cys Thr Leu Lys Pro Asn Thr Ile Phe Pro Asn Pro
 1               5                  10

<210> SEQ ID NO 24
<211> LENGTH: 12
<212> TYPE: PRT
<213> ORGANISM: Ictalurus punctatus

<400> SEQUENCE: 24

Cys Lys Leu Lys Glu Asn Asn Ile Phe Ser Lys Pro
 1               5                  10

<210> SEQ ID NO 25
<211> LENGTH: 12
<212> TYPE: PRT
<213> ORGANISM: Thunnus alalunga

<400> SEQUENCE: 25

Cys Thr Leu Lys Lys Asn Asn Val Phe Ser Arg Asp
 1               5                  10

<210> SEQ ID NO 26
<211> LENGTH: 12
<212> TYPE: PRT
<213> ORGANISM: Pleurogrammus monopterygius

<400> SEQUENCE: 26

Cys Thr Leu Arg Lys Asn Thr Val Phe Ser Arg Asp
 1               5                  10

<210> SEQ ID NO 27
<211> LENGTH: 12
<212> TYPE: PRT
<213> ORGANISM: Morone saxatilis

<400> SEQUENCE: 27

Cys Thr Leu Arg Lys Asn Ser Val Phe Ser Arg Asp
 1               5                  10

<210> SEQ ID NO 28
<211> LENGTH: 12
<212> TYPE: PRT
<213> ORGANISM: Cyprinus carpio

<400> SEQUENCE: 28

Cys Lys Leu Lys Glu Asn Asn Ile Phe Ser Lys Pro
 1               5                  10

<210> SEQ ID NO 29
<211> LENGTH: 12
<212> TYPE: PRT
<213> ORGANISM: Cyprinus carpio
```

```
<400> SEQUENCE: 29

Cys Thr Leu Lys Glu Asn Asn Ile Phe Ser Lys Pro
 1               5                  10

<210> SEQ ID NO 30
<211> LENGTH: 12
<212> TYPE: PRT
<213> ORGANISM: Muraenesox bagio

<400> SEQUENCE: 30

Cys Arg Leu Lys Asp Asn Lys Phe Phe Ser Lys Pro
 1               5                  10

<210> SEQ ID NO 31
<211> LENGTH: 12
<212> TYPE: PRT
<213> ORGANISM: Anguilla rostrata

<400> SEQUENCE: 31

Cys Arg Leu Gln Glu Asn Lys Ile Phe Ser Lys Pro
 1               5                  10

<210> SEQ ID NO 32
<211> LENGTH: 12
<212> TYPE: PRT
<213> ORGANISM: Homo sapiens

<400> SEQUENCE: 32

Cys Thr Leu Lys Glu Asn Pro Phe Phe Ser Gln Pro
 1               5                  10

<210> SEQ ID NO 33
<211> LENGTH: 12
<212> TYPE: PRT
<213> ORGANISM: Homo sapiens

<400> SEQUENCE: 33

Cys Thr Leu Gln Glu Asn Lys Phe Phe Ser Gln Pro
 1               5                  10

<210> SEQ ID NO 34
<211> LENGTH: 12
<212> TYPE: PRT
<213> ORGANISM: Homo sapiens

<400> SEQUENCE: 34

Cys Thr Leu Gln Glu Asn Pro Phe Phe Ser Lys Pro
 1               5                  10

<210> SEQ ID NO 35
<211> LENGTH: 12
<212> TYPE: PRT
<213> ORGANISM: Homo sapiens

<400> SEQUENCE: 35

Cys Thr Leu Gln Glu Asn Lys Phe Phe Ser Lys Pro
 1               5                  10

<210> SEQ ID NO 36
<211> LENGTH: 12
<212> TYPE: PRT
<213> ORGANISM: Homo sapiens

<400> SEQUENCE: 36

Cys Thr Leu Lys Glu Asn Lys Phe Phe Ser Lys Pro
 1               5                  10
```

```
1               5                   10

<210> SEQ ID NO 37
<211> LENGTH: 12
<212> TYPE: PRT
<213> ORGANISM: Homo sapiens

<400> SEQUENCE: 37

Cys Thr Leu Lys Lys Asn Lys Phe Phe Ser Lys Pro
1               5                   10
```

HUMAN LUTEINIZING HORMONE SUPERAGONISTS

RELATED APPLICATIONS

This application is a divisional of U.S. patent application Ser. No. 11/409,428, filed Apr. 21, 2006, now U.S. Pat. No. 7,687,610 which is a continuation of U.S. patent application Ser. No. 10/057,113, filed Jan. 25, 2002, now U.S. Pat. No. 7,070,788, which is a divisional of U.S. patent application Ser. No. 09/185,408, filed Nov. 3, 1998, now U.S. Pat. No. 6,361,992, which is a continuation of PCT/US96/06483 filed May 8, 1996, designating the United States of America and published in English as WO 97/42322 on Nov. 13, 1997, all of which are hereby expressly incorporated by reference in their entireties.

SEQUENCE LISTING

The present application is being filed along with a Sequence Listing in electronic format. The Sequence Listing is provided as a file entitled NIH147-1DC1D1_Sequence_Listing.txt, created Apr. 23, 2009, which is 7 Kb in size. The information in the electronic format of the Sequence Listing is incorporated herein by reference in its entirety.

FIELD OF THE INVENTION

This invention relates generally to modified glycoprotein hormones. Specifically, this invention relates to modifications to a human glycoprotein which create superagonist activity.

BACKGROUND OF THE INVENTION

Thyrotropin (thyroid-stimulating hormone, TSH) and the gonadotropins chorionic gonadotropin, (CG), lutropin (luteinizing hormone, LH), and follitropin (follicle-stimulating hormone, FSH) comprise the family of glycoprotein hormones. Each hormone is a heterodimer of two non-covalently linked subunits: α and β. Within the same species, the amino acid sequence of the α-subunit is identical in all the hormones, whereas the sequence of the β-subunit is hormone specific (Pierce, J. G. and Parsons, T. F. 1981 *Ann Rev Biochem* 50:465-495). The fact that the sequences of the subunits are highly conserved from fish to mammals implies that these hormones have evolved from a common ancestral protein (Fontaine Y-A. and Burzawa-Gerard, E. 1977 *Gen Comp Endocrinol* 32:341-347). Evolutionary changes of these hormones resulted in certain cases in modification of biological activity (Licht, P. et al. 1977 *Rec Progr Horm Res* 33:169-248 and Combarnous, Y. 1992 *Endocrine Rev* 13:670-691), although, specific structural determinants modulating biopotency have not been elucidated. For example, human thyroid stimulating hormone (hTSH) and bovine thyroid stimulating hormone (bTSH) share high homology in the α (70%) and β (89%) subunit sequence, but bTSH is 6-10 fold more potent than hTSH (Yamazaki, K. et al. 1995 *J Clin Endocrinol Metab* 80:473-479).

Glycoprotein hormones are crucial in certain therapies, such as in the treatment of patients with thyroid carcinoma (See, for example, Meier, C. A., et al. 1994 *J Clin Endocrinol Metabol* 78:22). The potential use of human thyroid stimulating hormone (TSH) in the treatment of this disease has been abandoned due to the potential transmission of Creutzfeldt-Jakob disease. An alternative to the use of human TSH is the use of bovine TSH, but this approach is very limited since this hormone causes side-effects such as nausea, vomiting, local induration, urticaria, and a relatively high possibility of anaphylactic shock (Meier, C. A., et al., supra). The lack of bioconsistency of urinary gonadotropins and the limited efficacy of recombinant glycoprotein hormones justify their further replacement with more effective recombinant analogs. Therefore, there is a need for human-derived glycoprotein hormones as well as agonists of these hormones.

For example the administration of an agonist of the thyroid stimulating hormone in a particular clinical situation such as thyroid carcinoma, will enhance the uptake of radioiodine into the carcinoma to treat the disease. Agonists of the thyroid stimulating hormone will cause a greater amount of the radioiodine to be targeted to the carcinoma, thereby resulting in a more effective treatment. Alternatively, glycoprotein hormones used to induce ovulation can be replaced with superagonists. This will lower the required dose of the hormone which currently is a major medical problem in fertility treatment (Ben-Rafael, Z., et al. 1995 *Fertility and Sterility* 63:689). Where the use of wild-type follicle stimulating hormone has led to hyperstimulation and higher rates of multiple pregnancies and abortions, apparently by a high number of hormone molecules stimulating many follicles, a superagonist of follicle-stimulating hormone can be administered to treat the infertility. The use of an agonist of this modified hormone can result in a lower frequency of stimulation of multiple follicles since a lower number of hormone molecules can be administered to achieve the desired result.

The present invention provides, for the first time, specific amino acid substitutions in human glycoprotein hormones which results in human glycoprotein hormone analogs that show a major increase in both in vitro and in vivo bioactivity.

SUMMARY OF THE INVENTION

In accordance with the purpose(s) of this invention, as embodied and broadly described herein, this invention, in one aspect, provides a human glycoprotein hormone comprising at least three basic amino acids in the α-subunit at positions selected from the group consisting of positions 11, 13, 14, 16, 17 and 20.

The invention further provides a human glycoprotein hormone comprising at least one basic amino acid in the α-subunit at positions selected from the group consisting of positions 11, 13, 14, 16, 17 and 20.

In another aspect, the invention provides a modified human glycoprotein hormone having increased activity over a wild-type human glycoprotein, wherein the modified human hormone comprises a basic amino acid substituted at a position corresponding to the same amino acid position in a non-human glycoprotein hormone having an increased activity over the wild-type human glycoprotein.

In another aspect, the invention provides a method of treating a condition associated with a glycoprotein hormone activity in a subject comprising administering a therapeutic amount of the glycoprotein hormone of the present invention to the patient.

In another aspect, the invention provides a method of constructing superactive nonchimeric analogs of human hormones comprising comparing the amino acid sequence of a more active homolog from another species to the human hormone, substituting amino acids in the human hormone with the corresponding amino acids from the other species, determining the activity of the substituted human hormone, and selecting superactive analogs from the substituted human hormones.

In yet another aspect, the present invention provides nucleic acids which encode the modified glycoprotein hormones.

BRIEF DESCRIPTION OF THE DRAWINGS

FIG. 1 shows a comparison of the relevant primary sequences of the α-subunit from 27 different species (a) Alignment of the subunit sequences obtained from sequencing of PCR amplified fragment of genomic DNA in chimpanzee, orangutan, gibbon and baboon (underlined), received from GeneBank, SWISS-PROT and PDB databank were made (SEQ ID NOs: 4-31). The numbering of the sequences corresponds to that of human α-subunit sequence (SEQ ID NO: 3). Dashes ( - - - ) indicate amino acid residues which are identical to those of the human α-subunit. Conserved among different species lysine residues are bolded. The primate sequences determined in this study are underlined. The human, chimpanzee and orangutan α-subunit sequences are the only sequences without basic amino acids in this region, despite the relatively high degree of similarity in diverse vertebrate species. (b) Mutations of human sequence made in this region included introduction of single and multiple Lys residues present in all non-human mammalian sequences (SEQ ID NOs: 32-37). Additionally, alanine mutagenesis of residues 13, 16 and 20 was used to study the role of Gln13, Pro16 and Gln20.

DETAILED DESCRIPTION OF THE PREFERRED EMBODIMENT

Figure 2A:
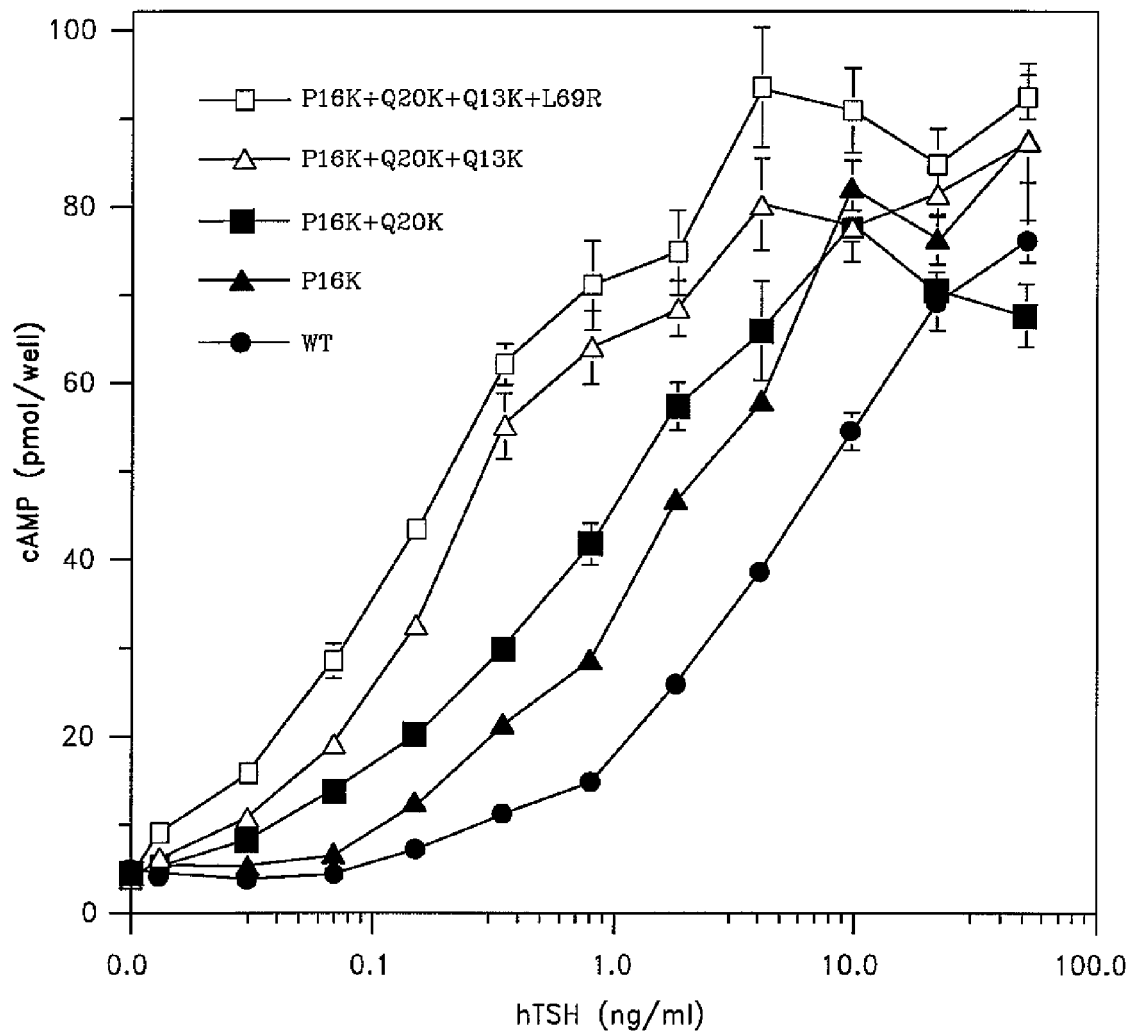
FIG. 2 shows the bioactivities and receptor binding activities of the most potent hTSH analogs: (a, b) cAMP stimulation in CHO-JP09 cells. Data represent the mean±SEM of triplicate determinations from a representative experiment repeated three (a) and two (b) times. (c, d) Receptor-binding activities to CHO-JP09 cells. The same mutants tested as in the FIG. 2a and FIG. 2b respectively. Values are the mean±SEM of quadruplicate determinations from one experiment, repeated two times. (e) Thymidine uptake stimulation in FRTL-5 cells. Values are the mean±SEM of quadruplicate determinations from one experiment, repeated two times. (I) Stimulation of $T_4$ secretion in mice. Each data point represents the mean±SEM of values from 4-5 animals of a representative experiment repeated two times. (g) cAMP stimulation in CHO-hTSH cells. Data represent the mean SEM of 3-4 determinations from a representative experiment repeated 3 times. (h) Receptor-binding activities in CHO-JP09 cells. Data represent the mean±SEM of 3-4 determinations from a representative experiment repeated 3 times. (i) Stimulation of $T_4$ secretion in mice. Each data point represents the mean±SEM of values from 4-5 animals of a representative experiment repeated two times.

The present invention may be understood more readily by reference to the following detailed description of the preferred embodiments of the invention and the Example included therein and to the Figures and their previous and following description.

Before the present compounds, compositions, and methods are disclosed and described, it is to be understood that this invention is not limited to specific hormones, specific subjects, i.e., humans as well as non-human mammals, specific amino acids, specific clinical conditions, specific analogs, or specific methods, as such may, of course, vary, and the numerous modifications and variations therein will be apparent to those skilled in the art. It is also to be understood that the terminology used herein is for the purpose of describing particular embodiments only and is not intended to be limiting.

As used in the specification and in the claims, "a" can mean one or more, depending upon the context in which it is used. Thus, for example, reference to "a human glycoprotein hormone" means that at least one human glycoprotein hormone is utilized.

In one aspect, the invention provides a human glycoprotein hormone comprising at least three basic amino acids in the α-subunit at positions selected from the group consisting of positions 11, 13, 14, 16, 17 and 20.

The invention further provides a human glycoprotein hormone comprising at least one basic amino acid in the α-subunit at positions selected from the group consisting of positions 11, 13, 14, 16, 17 and 20.

In another aspect, the invention provides a modified human glycoprotein hormone having increased activity over a wild-type human glycoprotein, wherein the modified human hormone comprises a basic amino acid substituted at a position corresponding to the same amino acid position in a non-human glycoprotein hormone having an increased activity over the wild-type human glycoprotein.

In another aspect, the invention provides a method of treating a condition associated with a glycoprotein hormone activity in a subject comprising administering a therapeutic amount of the glycoprotein hormone of the present invention to the patient.

In another aspect, the invention provides a method of assisting reproduction in a subject comprising administering an assisting amount of the glycoprotein hormone of the present invention.

In another aspect, the invention provides a method of constructing superactive nonchimeric analogs of human hormones comprising comparing the amino acid sequence of a more active homolog from another species to the human hormone, substituting amino acids in the human hormone with the corresponding amino acids from the other species, determining the activity of the substituted human hormone, and selecting superactive analogs from the substituted human hormones.

By "human" glycoprotein hormone is meant that the number of amino acid substitutions made in the wild-type sequence does not exceed one-half the number of amino acid differences at corresponding positions in the corresponding polypeptide hormones between human and another species. Thus, the modified polypeptide hormone would be considered more like the wild-type polypeptide hormone of the human than the corresponding polypeptide hormone from the non-human species from which the amino acid substitutions are derived, based on the amino acid coding sequence. For example, if there were a total of 20 amino acid differences at corresponding positions in corresponding glycoprotein hormones between a human glycoprotein and a bovine glycoprotein hormone, a "human" glycoprotein hormone would be a modified wild-type human hormone which contains 10 or fewer amino acid substitutions within its amino acid sequence which are homologous to the corresponding amino acids in the bovine amino acid sequence. More specifically, the thyroid stimulating hormone, as set forth in the Examples contained herein, would be considered "human" if 20 or more of the 40 total amino acid differences between the α- and β-subunits of the human and the bovine homologs are homologous to the amino acid at the corresponding position in the human thyroid stimulating hormone.

Naturally, because of the risk of an adverse immune response to the administration of the modified glycoprotein hormone where the recipient of the modified glycoprotein hormone is a human, the modified glycoprotein hormone is preferably homologous to the human amino acid sequence to the greatest extent possible without an unacceptable loss in the superagonist activity. Alternatively, where the subject being administered the modified glycoprotein is non-human, the modified glycoprotein hormone is preferably homologous to the specific non-human amino acid sequence to the greatest extent possible without an unacceptable loss in the superagonist activity. Thus, in a preferred embodiment of the present invention, in modifying a wild-type glycoprotein to construct a modified glycoprotein with a superagonist activity by substituting specific amino acids, the substituted amino acids which do not increase agonist activity number 10 or less, especially 9, 8, 7, 6, 5, 4, 3, and 2 or zero.

Likewise, by "nonchimeric" is meant that the number of amino substitutions does not exceed one-half the number of amino acid differences at corresponding positions in the corresponding polypeptide hormones between species, such that the modified polypeptide hormone would be considered more like the wild-type polypeptide hormone of the species being modified than the corresponding polypeptide hormone from the species from which the amino acid substitutions are derived, based on the amino acid coding sequence.

In yet another aspect, the present invention provides nucleic acids which encode the modified glycoprotein hormones.

Glycoprotein hormones comprise a family of hormones which are structurally related heterodimers consisting of a species-common α-subunit and a distinct β-subunit that confers the biological specificity for each hormone. For a general review of glycoprotein hormones, see, Pierce, J. G. et al. 1981 *Ann Rev Biochem* 50:465-495, see also Combarnous, Y. 1992 *Endocrine Rev* 13:670-691. This family of hormones includes chorionic gonadotropin (CG), lutropin (luteinizing hormone, LH), follitropin (follicle-stimulating hormone, FSH), and thyrotropin (thyroid-stimulating hormone, TSH). Each of these glycoprotein hormones with at least one basic amino acid in the β-subunit at positions selected from the group consisting of positions 11, 13, 14, 16, 17, and 20, is provided by the present invention.

Basic amino acids comprise the amino acids lysine, arginine, and histidine, and any other basic amino acid which may be a modification to any of these three amino acids, synthetic basic amino acids not normally found in nature, or any other amino acid which is positively charged at a neutral pH.

The glycoprotein hormones provided for by the present invention may be obtained in any number of ways. For example, a DNA molecule encoding a glycoprotein hormone can be isolated from the organism in which it is normally found. For example, a genomic DNA or cDNA library can be constructed and screened for the presence of the nucleic acid of interest. Methods of constructing and screening such libraries are well known in the art and kits for performing the construction and screening steps are commercially available (for example, Stratagene Cloning Systems, La Jolla, Calif.).

Once isolated, the nucleic acid can be directly cloned into an appropriate vector, or if necessary, be modified to facilitate the subsequent cloning steps. Such modification steps are routine, an example of which is the addition of oligonucleotide linkers which contain restriction sites to the termini of the nucleic acid. General methods are set forth in Sambrook et al. in *Molecular Cloning, a Laboratory Manual*, Cold Spring Harbor Laboratory Press (1989).

Once the nucleic acid sequence of the desired glycoprotein hormone is obtained, basic amino acids can be positioned at any particular amino acid positions by techniques well known in the art. For example, PCR primers can be designed which span the amino acid position or positions and which can substitute a basic amino acid for a non-basic amino acid. Then a nucleic acid can be amplified and inserted into the wild-type glycoprotein hormone coding sequence in order to obtain any of a number of possible combinations of basic amino acids at any position of the glycoprotein hormone. Alternatively, one skilled in the art can introduce specific mutations at any point in a particular nucleic acid sequence through techniques for point mutagenesis. General methods are set forth in Smith, M 1985 *Ann Rev Gen* 19:423-462 and Zoller, M. J. 1991 *Curr Opin Struct Biol* 1:605-610.

Another example of a method of obtaining a DNA molecule encoding a specific glycoprotein hormone is to synthesize a recombinant DNA molecule which encodes the glycoprotein hormone. For example, oligonucleotide synthesis procedures are routine in the art and oligonucleotides coding for a particular protein region are readily obtainable through automated DNA synthesis. A nucleic acid for one strand of a double-stranded molecule can be synthesized and hybridized to its complementary strand. One can design these oligonucleotides such that the resulting double-stranded molecule has either internal restriction sites or appropriate 5' or 3' overhangs at the termini for cloning into an appropriate vector. Double-stranded molecules coding for relatively large proteins can readily be synthesized by first constructing several different double-stranded molecules that code for particular regions of the protein, followed by ligating these DNA molecules together. For example, Cunningham, et al. 1989 *Science* 243:1330-1336, have constructed a synthetic gene encoding the human growth hormone gene by first constructing overlapping and complementary synthetic oligonucleotides and ligating these fragments together. See also, Ferretti, et al. 1986 *Proc Nat Acad Sci U.S.A.* 82:599-603, wherein synthesis of a 1057 base pair synthetic bovine rhodopsin gene from synthetic oligonucleotides is disclosed. By constructing a glycoprotein hormone in this manner, one skilled in the art can readily obtain any particular glycoprotein hormone with basic amino acids at any particular position or positions of either the α-subunit, the β-subunit, or both. See also, U.S. Pat. No. 5,503,995 which describes an enzyme template reaction method of making synthetic genes. Techniques such as this are routine in the art and are well documented. DNA fragments encoding glycoprotein hormones can then be expressed in vivo or in vitro as discussed below.

Once a nucleic acid encoding a particular glycoprotein hormone of interest, or a region of that nucleic acid, is constructed, modified, or isolated, that nucleic acid can then be cloned into an appropriate vector, which can direct the in vivo or in vitro synthesis of that wild-type and/or modified glycoprotein hormone. The vector is contemplated to have the necessary functional elements that direct and regulate transcription of the inserted gene, or hybrid gene. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al., supra).

There are numerous E. coli (Escherichia coli) expression vectors known to one of ordinary skill in the art which are useful for the expression of the nucleic acid insert. Other microbial hosts suitable for use include bacilli, such as Bacillus subtilis, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, an amino terminal methionine can be provided by insertion of a Met codon 5' and in-frame with the downstream nucleic acid insert. Also, the carboxy-terminal extension of the nucleic acid insert can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MF"-1 gene) is routinely used to direct protein secretion from yeast (Brake, et al. 1984 *Proc Nat Acad Sci U.S.A.* 81:4642-4646). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage signal sequence. The nucleic acid coding sequence can be fused in-frame to the pre-pro-alpha-factor leader region. This construct is then put under the control of a strong transcription promoter, such as the alcohol dehydrogenase I promoter or a glycolytic promoter. The nucleic acid coding sequence is followed by a translation termination codon which is followed by transcription termination signals. Alternatively, the nucleic acid coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast. Efficient post translational glycosolation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of active proteins in mammalian cells are characterized by insertion of the protein coding sequence between a strong viral promoter and a polyadenylation signal. The vectors can contain genes conferring hygromycin resistance, gentamicin resistance, or other genes or phenotypes suitable for use as selectable markers, or methotrexate resistance for gene amplification. The chimeric protein coding sequence can be introduced into a Chinese hamster ovary (CHO) cell line using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, or lipofectin mediated transfection or electroporation maybe used for other cellular hosts.

Alternative vectors for the expression of genes in mammalian cells, those similar to those developed for the expression of human gamma-interferon, tissue plasminogen activator, clotting Factor VRIII, hepatitis B virus surface antigen, protease Nexinl, and eosinophil major basic protein, can be employed. Further, the vector can include CMV promoter sequences and a polyadenylation signal available for expression of inserted nucleic acids in mammalian cells (such as COS-7). Expression of the gene or hybrid gene can be by either in vivo or in vitro. In vivo synthesis comprises transforming prokaryotic or eukaryotic cells that can serve as host cells for the vector. An example of modified glycoprotein hormones inserted into a prokaryotic expression vector is given in the Example section contained herein.

Alternatively, expression of the gene can occur in an in vitro expression system. For example, in vitro transcription systems are commercially available which are routinely used to synthesize relatively large amounts of mRNA. In such in vitro transcription systems, the nucleic acid encoding the glycoprotein hormone would be cloned into an expression vector adjacent to a transcription promoter. For example, the Bluescript II cloning and expression vectors contain multiple cloning sites which are flanked by strong prokaryotic transcription promoters (Stratagene Cloning Systems, La Jolla, Calif.). Kits are available which contain all the necessary reagents for in vitro synthesis of an RNA from a DNA template such as the Bluescript vectors (Stratagene Cloning Systems, La Jolla, Calif.). RNA produced in vitro by a system such as this can then be translated in vitro to produce the desired glycoprotein hormone (Stratagene Cloning Systems, La Jolla, Calif.).

Another method of producing a glycoprotein hormone is to link two peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry (Applied Biosystems, Inc., Foster City, Calif.). One skilled in the art can readily appreciate that a peptide or polypeptide corresponding to a hybrid glycoprotein hormone can be synthesized by standard chemical reactions. For example, a peptide or polypeptide can be synthesized and not cleaved from its synthesis resin whereas the other fragment of a hybrid peptide can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a hybrid peptide. (Grant, G. A. in *Synthetic Peptides: A User Guide*, W.H. Freeman and Co., N.Y. (1992) and Bodansky, M. and Trost, B., Ed., in *Principles of Peptide Synthesis*, Springer-Verlag Inc., N.Y. (1993)). Alternatively, the peptide or polypeptide can by independently synthesized in vivo as described above. Once isolated, these independent peptides or polypeptides may be linked to form a glycoprotein hormone via similar peptide condensation reactions.

For example, enzymatic ligation of cloned or synthetic peptide segments can allow relatively short peptide fragments to be joined to produce larger peptide fragments, polypeptides or whole protein domains (Abrahmsen, L., et al., 1991 *Biochemistry* 30:4151). Alternatively, native chemical ligation of synthetic peptides can be utilized to synthetically construct large peptides or polypeptides from shorter peptide fragments. This method consists of a two step chemical reaction (Dawson, et al., 1994 *Science* 266:776-779). The first step is the chemoselective reaction of an unprotected synthetic peptide-α-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini, et al. 1987 *FEBS Lett* 307: 97, Clark-Lewis, I., et al. 1994 *J Biol Chem* 269:16075, Clark-Lewis, L, et al. 1991 *Biochemistry* 30:3128, and Clore, et al. 1994 *Biochemistry* 29:1689).

Alternatively, unprotected peptide segments can be chemically linked where the bond formed between the peptide segments as a result of the chemical ligation is an unnatural (non-peptide) bond (Schnolzer, M, et al. 1992 *Science* 256: 221). This technique has been used to synthesize analogs of protein domains as well as large amounts of relatively pure proteins with full biological activity (deLisle Milton, R. C., et al. in *Techniques in Protein Chemistry IV*, Academic Press, New York, pp. 257-267 (1992)).

The invention also provides fragments of modified glycoprotein hormones which have either superagonist or antagonist activity. The polypeptide fragments of the present invention can be recombinant proteins obtained by cloning nucleic acids encoding the polypeptide in an expression system capable of producing the polypeptide fragments thereof. For example, one can determine the active domain of a glycoprotein hormone which, together with a β-subunit, can interact with a glycoprotein hormone receptor and cause a biological effect associated with the glycoprotein hormone. In one example, amino acids found to not contribute to either the activity or the binding specificity or affinity of the glycproprotein hormone can be deleted without a loss in the respective activity.

For example, amino or carboxy-terminal amino acids can be sequentially removed from either the native or the modified glycoprotein hormone and the respective activity tested in one of many available assays. In another example, a fragment of a modified glycoprotein can comprise a modified hormone wherein at least one amino acid has been substituted for the naturally occurring amino acid at specific positions in either the α or the β-subunit, and a portion of either amino terminal or carboxy terminal amino acids, or even an internal region of the hormone, has been replaced with a polypeptide fragment or other moiety, such as biotin, which can facilitate in the purification of the modified glycoprotein hormone. For example, a modified glycoprotein can be fused to a maltose binding protein, through either peptide chemistry of cloning the respective nucleic acids encoding the two polypeptide fragments into an expression vector such that the expression of the coding region results in a hybrid polypeptide. The hybrid polypeptide can be affinity purified by passing it over an amylose affinity column, and the modified glycoprotein can then be separated from the maltose binding region by cleaving the hybrid polypeptide with the specific protease factor Xa. (See, for example, New England Biolabs Product Catalog, 1996, pg. 164).

Active fragments of a glycoprotein hormone can also be synthesized directly or obtained by chemical or mechanical disruption of larger glycoprotein hormone. An active fragment is defined as an amino acid sequence of at least about 5 consecutive amino acids derived from the naturally occurring amino acid sequence, which has the relevant activity, e.g., binding or regulatory activity.

The fragments, whether attached to other sequences or not, can also include insertions, deletions, substitutions, or other selected modifications of particular regions or specific amino acids residues, provided the activity of the peptide is not significantly altered or impaired compared to the modified glycoprotein hormone. These modifications can provide for some additional property, such as to remove/add amino acids capable of disulfide bonding, to increase its bio-longevity, etc. In any case, the peptide must possess a bioactive property, such as binding activity, regulation of binding at the binding domain, etc. Functional or active regions of the glycoprotein hormone may be identified by mutagenesis of a specific region of the hormone, followed by expression and testing of the expressed polypeptide. Such methods are readily apparent to a skilled practitioner in the art and can include site-specific mutagenesis of the nucleic acid encoding the receptor (Zoller, M. J. et al., supra).

In one embodiment of the present invention, the human glycoprotein hormone comprises at least one basic amino acid in the α-subunit at the position selected from the group consisting of positions 11, 13, 14, 16, 17, and 20. In one embodiment, the human glycoprotein hormone has a basic amino acid at position 11. In another embodiment, the human glycoprotein hormone has a basic amino acid at position 13. In another embodiment, the human glycoprotein hormone has a basic amino acid at position 14. In another embodiment, the human glycoprotein hormone has a basic amino acid at position 16. In another embodiment, the human glycoprotein hormone has a basic amino acid at position 17. In another embodiment, the human glycoprotein hormone has a basic amino acid at position 20. In another embodiment of the present invention, the basic amino acid at position 11, 13, 14, 16, and 20 is lysine. In yet another embodiment of the present invention, the basic amino acid at position 17 is arginine.

The present invention also provides for a human glycoprotein hormone with basic amino acids in the α-subunit in all combinations of any two positions selected from the group consisting of positions 11, 13, 14, 16, 17, and 20. For example, basic amino acids may be present at positions 11 and 13, or positions 11, and 14, or positions 11 and 16, or positions 11 and 17, or positions 11 and 20, or positions 13 and 14, or positions 13 and 17, or positions 14 and 16, or positions 14 and 17, or positions 14 and 20, or positions 16 and 17, or positions 17 and 20. In one embodiment of the present invention, the human glycoprotein hormone has basic amino acids at position 16 and 13. In another embodiment of the present invention, the human glycoprotein hormone has basic amino acids at positions 20 and 13. In yet another embodiment, the human glycoprotein hormone has basic amino acids at positions 16 and 20.

The present invention also provides for a human glycoprotein hormone with basic amino acids in the α-subunit in all combinations of any three positions selected from the group consisting of positions 11, 13, 14, 16, 17, and 20. For example, basic amino acids may be present at positions 11, 13, and 14, or positions 11, 13, and 16, or positions 11, 13, and 17, or positions 11, 13, and 20, or positions 11, 14, and 16, or positions 11, 14, and 17, or positions 11, 14, and 20, or positions 11, 16, and 17, or positions 11, 16, and 20, or positions 11, 17, and 20, or positions 13, 14, and 16, or positions 13, 14, and 17, or positions 13, 14, and 20, or positions 13, 16, and 17, or positions 13, 17, and 20, or positions 14, 16, and 17, or positions 14, 16, and 20, or positions 14, 17, and 20, or positions 16, 17, and 20. In a preferred embodiment of the present invention, the human glycoprotein hormone has basic amino acids at positions 13, 16, and 20. In another embodiment of the present invention, the hormone is thyroid stimulating hormone. In another embodiment of the present invention, the hormone is follicle-stimulating hormone. In another embodiment of the present invention, the hormone is luteinizing hormone. In another embodiment of the present invention, the hormone is chorionic gonadotropin. In yet another embodiment of the present invention, the basic amino acids at any three positions selected from the group consisting of positions 11, 13, 14, 16, 17, and 20, are lysine.

The present invention also provides for a human thyroid stimulating hormone with at least three basic amino acids in the α-subunit at positions selected from the group consisting of positions 11, 13, 14, 16, 17, and 20, where the thyroid stimulating hormone also has a basic amino acid in at least one position selected from the group consisting of positions 58, 63, and 69 of the β-subunit. In one embodiment of the present invention, the thyroid stimulating hormone has a basic amino acid in at position 58 of the β-subunit. In another embodiment of the present invention, the thyroid stimulating hormone has a basic amino acid in at position 63 of the β-subunit. In another embodiment of the present invention, the thyroid stimulating hormone has a basic amino acid in at position 69 of the β-subunit. In another embodiment of the present invention, the thyroid stimulating hormone has a basic amino acid in each of positions 58, 63, and 69 of the β-subunit. In yet another embodiment of the present invention, the basic amino acid in at least one position selected from the group consisting of positions 58, 63, and 69 of the β-subunit is arginine.

The present invention also provides for a human glycoprotein hormone with basic amino acids in the α-subunit in all combinations of any four positions selected from the group consisting of positions 11, 13, 14, 16, 17, and 20. One skilled in the art will readily determine the possible combinations available. In one embodiment, the human glycoprotein hormone has basic amino acids at positions 11, 13, 16, and 20. In another embodiment, the human glycoprotein hormone has basic amino acids at positions 11, 13, 17, and 20. In another embodiment, the human glycoprotein hormone has basic amino acids at positions 13, 14, 17, and 20. In a preferred embodiment, the human glycoprotein hormone has basic amino acids at positions 13, 14, 16, and 20. In yet another embodiment of the present invention, the basic amino acids at any four positions selected from the group consisting of positions 11, 13, 14, 16, 17, and 20, are lysine.

The present invention also provides for a human glycoprotein hormone with basic amino acids in the α-subunit in all combinations of any five positions selected from the group consisting of positions 11, 13, 14, 16, 17, and 20. One skilled in the art will readily determine the possible combinations available. In one embodiment, the human glycoprotein hormone has basic amino acids at positions 13, 14, 16, 17, and 20. In another embodiment, the human glycoprotein hormone has basic amino acids at positions 11, 13, 14, 16, and 20. In yet another embodiment of the present invention, the basic amino acids at any five positions selected from the group consisting of positions 11, 13, 14, 16, 17, and 20, are selected from the group consisting of lysine and arginine.

The present invention also provides for a human glycoprotein hormone with basic amino acids in the α-subunit in all six of positions 11, 13, 14, 16, 17, and 20.

In another aspect, the present invention provides a human glycoprotein hormone with a basic amino acid in the α-subunit in at least one position selected from the group consisting of positions 11, 13, 14, 16, 17, and 20, wherein the hormone is human thyroid stimulating hormone and there is a basic amino acid in at least one position selected from the group consisting of positions 58, 63, and 69 of the β-subunit. In one embodiment of the present invention, the human glycoprotein hormone has a basic amino acid at position 58 of the β-subunit of the human thyroid stimulating hormone. In another embodiment of the present invention, the human glycoprotein hormone has a basic amino acid at position 63 of the β-subunit of the human thyroid stimulating hormone. In a preferred embodiment of the present invention, the human glycoprotein hormone has a basic amino acid at position 69 of the β-subunit of the human thyroid stimulating hormone. In another embodiment of the present invention, the human glycoprotein hormone has basic amino acids at position 58, 63, and 69 of the β-subunit of the human thyroid stimulating hormone. In yet another embodiment of the present invention, the basic amino acid at the position selected from the group consisting of positions 58, 63, and 69 is arginine.

In another aspect, the present invention provides a human follicle-stimulating hormone, a human luteinizing hormone, or a human chorionic gonadotropin glycoprotein hormone, wherein the hormone comprises a basic amino acid in at least one position selected from the group consisting of positions in the β-subunit of any of the glycoprotein hormones, corresponding to positions 58, 63, and 69 of the β-subunit of the human thyroid stimulating hormone. This approach applies equally to non-humans as well. For example, the β-subunit amino acid sequences of two bovine glycoprotein hormones can be compared and substitutions made to any of the subunits based on the sequence differences.

One skilled in the art can readily determine which sites of the β-subunits of the other glycoprotein hormones correspond to sites 58, 63, and 69 of the β-subunit of the human thyroid stimulating hormone. For example, see Ward, et al. in *Structure-function relationships of gonadotropins*, Bellet, D and Bidard, J. M. (eds) Serono Symposium Publications, Raven Press, New York, 65:1-19 (1990), where the amino acid sequences of 26 various glycoprotein hormone β-subunits are aligned and compared. Therefore, one skilled in the art can readily substitute non-basic amino acids at these sites of the other glycoprotein hormones for basic amino acids.

Similarly, the present invention provides for any human glycoprotein, wherein the hormone comprises a basic amino acid in at least one position selected from the group consisting of positions in the β-subunit of a glycoprotein hormone corresponding to the same positions in any of the other human glycoprotein hormones. For example, the amino acid sequence of the β-subunits of the human luteinizing hormone and the human chorionic gonadotropin hormone can be compared and amino acid substitutions made at selected sites in either of these glycoptotein hormones based on the amino acid differences between the two β-subunits. This approach also applies equally to non-humans as well.

The present invention also provides a modified human glycoprotein hormone having increased activity over a wild-type human glycoprotein, wherein the modified human hormone comprises a basic amino acid substituted at a position corresponding to the same amino acid position in a non-human glycoprotein hormone having an increased activity over the wild-type human glycoprotein.

The non-human glycoprotein hormone having an increased activity over the wild-type human glycoprotein can be any non-human species. For example, the non-human species can be bovine. See, for example, Benua, R. S., et al. 1964 *J Nucl Med* 5:796-801 and Hershman, J. M., et al. 1972 *J Clin Endocrinol Metab* 34:814-818. Alternatively, the non-human species can be equine, porcine, ovine, and the like. In the Example contained herein, the sequence of the 10-21 amino acid region of 27 species is set forth.

The present invention also provides a modified glycoprotein hormone having increased activity over a wild-type glycoprotein hormone from the same species, wherein the modified glycoprotein hormone comprises a basic amino acid substituted at a position corresponding to the same amino acid position in a glycoprotein hormone from another species having an increased activity over the wild-type glycoprotein hormone. Therefore the glycoprotein being modified to increase its activity can be from a non-human species. For example, one can compare porcine glycoprotein hormones to bovine glycoprotein hormones, design porcine glycoprotein hormones with amino acid substitutions at positions where the porcine and the bovine sequences are different, construct porcine glycoprotein hormones with the selected changes, and administer the modified porcine glycoprotein hormone to porcine animals. Alternatively, the glycoprotein hormone being modified can be bovine.

The present invention also provides a modified glycoprotein hormone having increased activity over the wild-type glycoprotein hormone from the same species, wherein the modified glycoprotein hormone comprises a basic amino acid substituted at a position corresponding to the same amino acid position in a different glycoprotein hormone from the same species having an increased activity over the wild-type glycoprotein hormone. For example, the β-subunits of human thyroid-stimulating hormone and human chorionic gonadotropin can be compared and amino acid substitutions to either of these β-subunits can be made based on any sequence divergence. Naturally, only those changes which generally increase or decrease the activity of the modified glycoprotein hormone are contemplated since the hormone receptor specificity will still need to be retained. An example of such a β-subunit modification is set forth in the Examples contained herein, where basic amino acids were substituted at positions 58 and 63 of the human thyroid stimulating hormone based on sequence comparison between the human thyroid stimulating hormone and the human chorionic gonadotropin hormone.

Modification refers to the substitution of a non-basic amino acid at any particular position or positions of the wild-type glycoprotein with a basic amino acid. In a presently preferred embodiment of the present invention, these modifications comprise the substitution of lysine for a non-basic amino acid.

The effect of the modification or modifications to the wild-type glycoprotein hormone can be ascertained in any number of ways. For example, cyclic AMP (cAMP) production in cells transfected with the modified glycoprotein can be measured and compared to the cAMP production of similar cells transfected with the wild-type glycoprotein hormone. Alternatively, progesterone production in cells transfected with the modified glycoprotein can be measured and compared to the progesterone production of similar cells transfected with the wild-type glycoprotein hormone. Alternatively, the activity of a modified glycoprotein hormone can be determined from receptor binding assays, from thymidine uptake assays, or from $T_4$ secretion assays. Specific examples of such assays for determining the activity of modified glycoprotein hormones is set forth in the Example section contained herein. One skilled in the art can readily determine any appropriate assay to employ to determine the activity of either a wild-type or a modified glycoprotein hormone.

In one embodiment of the present invention, the modified glycoprotein hormone has an activity which is increased over the activity of the wild type glycoprotein hormone by at least 3 fold. This increased activity can be assessed by any of the techniques mentioned above and described in the Example contained herein, or in any other appropriate assay as readily determined by one skilled in the art. The increased activity does not have to be consistent from assay to assay, or from cell line to cell line, as these of course, will vary. For example, and as set forth in the Example contained herein, the relative potency of the P16K mutation in the α-subunit of the human glycoprotein hormone compared to the activity of the wild type glycoprotein hormone in a cAMP assay was approximately 6.4 fold higher. In the progesterone release assay, however, the difference between the same mutant and the wild-type glycoprotein hormone was approximately 3.4 fold in potency and 1.6 fold in Vmax. This specific modification demonstrates at least a 3 fold increase in activity in at least one assay, and therefore represents a glycoprotein hormone with at least a 3 fold increase in activity.

To modify additional amino acid positions, glycoprotein hormone sequences from human and non-humans can be aligned using standard computer software programs such as DNASIS (Hitachi Software Engineering Co. Ltd.). The amino acid residues that differ between the human and the non-human glycoprotein hormone can then be substituted using one of the above-mentioned techniques, and the resultant glycoprotein hormone assayed for its activity using one of the above-mentioned assays.

The subject being treated or administered a modified glycoprotein hormone can be a human or any non-human mammal. For example, the modified glycoprotein hormone superagonists may be used in the superovulation of bovine animals by administering these glycoprotein hormones to those bovine animals.

The methods used in substituting a basic amino acid for a non-basic amino acid at any particular position or positions can also be used to design glycoprotein hormone antagonists. By making specific substitutions and monitoring the activity of these modified glycoprotein hormones, one can determine which modifications yield glycoprotein hormones with reduced activity. These glycoprotein hormone agonists can be used in studies of the hormone receptor such as receptor turnover rates, receptor affinity for the glycoprotein hormone, or even in therapeutic procedures such as treatment of Grave's disease and in fertility control.

The present invention also provides a method of treating a condition associated with a glycoprotein hormone activity in a subject comprising administering a therapeutic amount of the glycoprotein hormone of the present invention to the subject. These conditions include any condition associated with a glycoprotein hormone activity. Examples of these conditions include, but are not limited to, ovulatory disfunction, luteal phase defect, unexplained infertility, male factor infertility, time-limited conception.

In another example, the glycoprotein hormone may be administered to diagnose and treat a thyroid carcinoma. For example, the administration of bovine TSH to a human subject can be used to stimulate the uptake of $^{131}$I in thyroid tissue to treat thyroid carcinoma (Meier, C. A., et al. 1994 *J Clin Endocrinol Metabol* 78:22).

A skilled practitioner in the art can readily determine the effective amount of the glycoprotein hormone to administer and will depend on factors such as weight, size, the severity of the specific condition, and the type of subject itself. The therapeutically effective amount can readily be determined by routine optimization procedures. The present invention provides glycoprotein hormones with increased activity relative to the wild-type glycoprotein hormone. These modified glycoprotein hormones will allow a skilled practitioner to administer a lower dose of a modified glycoprotein hormone relative to the wild-type glycoprotein hormones to achieve a similar therapeutic effect, or alternatively, administer a dose of the modified glycoprotein hormone similar to the dose of the wild-type glycoprotein hormone to achieve an increased therapeutic effect.

Depending on whether the glycoprotein hormone is administered orally, parenterally, or otherwise, the administration of the prostaglandin can be in the form of solid, semi-solid, or liquid dosage forms, such as, for example, tablets, pills, capsules, powders, liquids, creams, and suspensions, or the like, preferably in unit dosage form suitable for delivery of a precise dosage. The glycoprotein hormone may include an effective amount of the selected glycoprotein hormone in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected glycoprotein hormone without causing unacceptable biological effects or interacting in an unacceptable manner with the glycoprotein hormone. Actual methods of preparing such dosage forms are known, or will be apparent, to those skilled in this art; for example, see Remington's Pharmaceutical Sciences, latest edition (Mack Publishing Co., Easton, Pa.).

In another aspect, the present invention provides a method of assisting reproduction in a subject comprising administering an assisting amount of the glycoprotein hormone of the present invention. For example, in a subject with isolated gonadotropin deficiency (IGD), administration of modified follicle stimulating hormone (follitropin) and luteinizing hormone (lutropin) may be administered to the subject to restore normal gonadal function. It is widely known in the art that glycoprotein hormones such as FSH and LH are integral in female reproductive physiology, and these glycoprotein hormones may be administered to a subject to overcome a number of reproductive disorders and thereby assist reproduction.

Genetic therapy is another approach for treating hormone disorders with the modified glycoprotein hormones of the present invention. In this approach, a gene encoding the modified glycoprotein hormone can be introduced into a cell, such as a germ line cell or a somatic cell, so that the gene is expressed in the cell and subsequent generations of those cells are capable of expressing the introduced gene. For example, any particular gonadotropin hormone can be inserted into an ovarian cell, or its precursor, to enhance ovulation. Alternatively, introducing thyroid cells carrying a gene encoding a superagonist of the thyroid stimulating hormone into an individual with thyroid carcinoma can obviate the need for continual administration of TSH for stimulating radioiodine uptake in the thyroid carcinoma. Suitable vectors to deliver the coding sequence are well known in the art. For example, the vector could be viral, such as adenoviral, adenoassociated virus, retrovirus, or non-viral, such as cationic liposomes.

The modified glycoprotein hormones as provided by the present invention can also be used for targeting delivery of therapeutic agents to thyroid tissues or gonadal tissue, or in the treatment of certain neoplasms.

In yet another aspect, the invention provides a method of constructing superactive nonchimeric analogs of human hormones comprising comparing the amino acid sequence of a more active homolog from another species to the human hormone, substituting amino acids in the human hormone with the corresponding amino acids from the other species, determining the activity of the substituted human hormone, and selecting superactive analogs from the substituted human hormones. Superactive analogs of human hormones includes any analog whose activity is increased over the corresponding activity of the wild-type hormone. For example, the modification of the human thyroid stimulating hormone at position 11 in the α-subunit from threonine to lysine (T11K) results in a relative increase in the cAMP production in JP09 cells cultured in vitro. (See Table II as set forth in the Example contained herein). This modification of the human thyroid stimulating hormone therefore results in a superactive analog of the wild-type human thyroid stimulating hormone. The specific amino acid or amino acids to substitute to create the modification can be determined, as discussed above, by: determining the activity of the homolog from another species and comparing that activity to the human hormone; then comparing the aligned sequences to determine the amino acid sequence differences; then substituting the appropriate amino acid in the hormone from another species for the amino acid at the corresponding position in the human hormone; then determining the activity of the modified human hormone by one of the above-mentioned techniques; and then comparing the activity of the modified human hormones to the wild-type human hormone, thereby selecting the superactive analogs from the substituted human hormones.

All combinations of amino acid substitutions may be utilized to obtain a glycoprotein superagonist. For example, neutral amino acids can be substituted for basic or acidic amino acids. Alternatively, basic amino acids can be substituted for acidic or neutral amino acids, or acidic amino acids may be substituted for neutral or basic amino acids. One skilled in the art will recognize, as discussed above, that substitution of one amino acid for another can be at either the nucleic acid level in the nucleotide sequence that encodes the glycoprotein hormone or part of the glycoprotein hormone, or at the polypeptide level. Any human hormone can be modified by this method and its superactive analogs selected. In particular, the human hormone can be a glycoprotein hormone.

EXAMPLES

The sequence between Cys10 and Pro21 of the human α-subunit was selected as the primary target for mutagenesis (FIG. 1). hCG-based homology modeling suggested that this region of the α-subunit is distant from the β-subunit in all glycoprotein hormones, contains several surface-exposed residues and includes a single turn of a $3_{10}$-helix between Pro16 and Ser19 (Wu, H. et al. 1994 *Structure* 2:545-558). The human α-subunit differs from bovine in position 11, 13, 16, 17 and 20 (FIG. 1 *a*) and four of these changes are nonconservative (Thr11→Lys, Gln13→Lys, Pro16→Lys and Gln20→Lys). We used PCR amplification to determine the sequence of the 11-20 region in the α-subunit of several primates including higher apes (common chimpanzee—*Pan troglodytes*, orangutan—*Pongo pygmaeus*), lesser apes (gibbon—*Hylobates* sp.), Old World monkey (baboon—*Papio anubis*) and compare them with previously known mammalian sequences including rhesus macaque (*Macaca mulatta*; Old World monkey), common marmoset (*Callithrix jacchus*; New World monkey) and human (FIG. 1 a). Simultaneous comparison of the sequences between different species suggested that basic residues in this region were replaced relatively late in primate evolution. The Rhesus monkey α-subunit gene codes for Lys residues at positions 11, 16 and 20 and an Arg residue at position 13 (Golos, T. G. et al. 1991 *DNA Cell Biol* 10:367-380), the baboon sequence codes for Gln at position 16, whereas gibbon sequence contains only one weakly basic imidazolium group of His at position 13 (FIG. 1 a). Apparently a cluster of positively charged amino acids in this region was maintained and modified during vertebrate evolution, but is not present in the higher apes and human sequence. The gradual elimination of positively charged residues in the 11-20 region of α-subunit coincide with the evolutionary divergence of the hominoids (human and apes) from the Old World monkeys. Our hypothesis that this region may modulate binding to the receptor was further supported by: 1) the highest reactivity of Tyr21 in bTSH toward iodination (Stanton, P. G. and Hearn, M. T. W. 1987 *J Biol Chem* 262: 1623-1632), 2) mapping of antigenic determinants in hCG (Dirnhofer S. et al. 1994 *J Endocrinol* 140:145-154), 3) the role of amino groups of Lys in the ovine and human α-subunit for effective hormone-receptor interaction as studied by acylation (Liu, W. K. et al. 1974 *J Biol Chem* 249:5544-5550), labeling with acetic anhydride (Yadav, S. P. et al. 1994 *Mol Endocrinol* 8:1547-1558) and pegylation of individual subunits.

Consequently, positively charged Lys residues were inserted into the Cys10-Pro21 region of the human α-subunit (FIG. 1 b). Two other regions were also mutagenized (Table I). A single nonconservative Leu69→Arg mutation in the TSHβ-subunit was made based on a similar sequence comparison.

Effects of Mutations

Cotransfection of wild-type (WT) or mutant human α and hTSHβ (Joshi, L. et al. 1995 *Endocrinology* 136:3839-3848) or hCGβ cDNAs in various combination into CHO-K1 cells resulted in the expression of 14 hTSH and 11 hCG heterodimers (Table I). In contrast to many other mutagenesis studies (Ji, I., 1993 *Biol Chem* 268:22971-22974; Grossmann, M. et al. 1995 *Mol Endocrinol* 9:948-958) the expression of mutants was generally comparable to the WT. The following hTSH α-mutants were expressed at levels higher than WT-hTSH: T11K, Q13K, P16K, Q20K, Q50P and Q13K⁺ P16K+Q20K. Thus, this set of evolutionary justified mutations did not impair, in a major way, synthesis of the hTSH or hCG molecule, but may facilitate in certain cases hormone production.

Various bioassays were used to compare the relative potency and efficacy of hTSH and hCG mutants. The ability of WT and mutant hTSH to stimulate cAMP production was tested in CHO-JP09 cells with stably transfected human TSH receptor. This assay revealed the following order of potencies in single α-subunit mutants: P16K (6-fold lower $EC_{50}$ than WT)≧Q20K>Q13K>T11K>WT-hTSH≈Q50P≈R67K (Table II). Receptor binding activity of WT and mutants hTSH was assessed in a competitive binding assay to porcine thyroid membranes. Consistent with the cAMP stimulation, the following order of potencies was observed: P16K (5-fold greater affinity than WT)>Q20K≧Q13K>T11K>WT-hTSH≈Q50P≈R67K (Table II). Thus, the increase in potency of single mutants observed in JP09 cells was directly correlated with the increase of affinity to the TSH receptor. Most notably, each mutation to a Lys residue in the 11-20 region caused a substantial increase in activity, but changes outside this critical region had no (R67K, Q50P) effect on receptor binding affinity and bioactivity (Table II). Alanine mutagenesis of amino acids 13, 16 and 20 in hTSH did not significantly alter hormone activity, indicating that only selective reconstitution of basic amino acids present in homologous hormones of other species resulted in the functional changes. Moreover, the exchange of αSer43 to Arg and the replacements of αHis90 and αLys91 showed that these residues were less important for hTSH than for hCG bioactivity, emphasizing hormone- and site-specific roles of basic residues (Grossmann, M. et al. 1995 *Mol Endocrinol* 9:948-958).

Superagonists with Combined Mutations

Figure 2B:
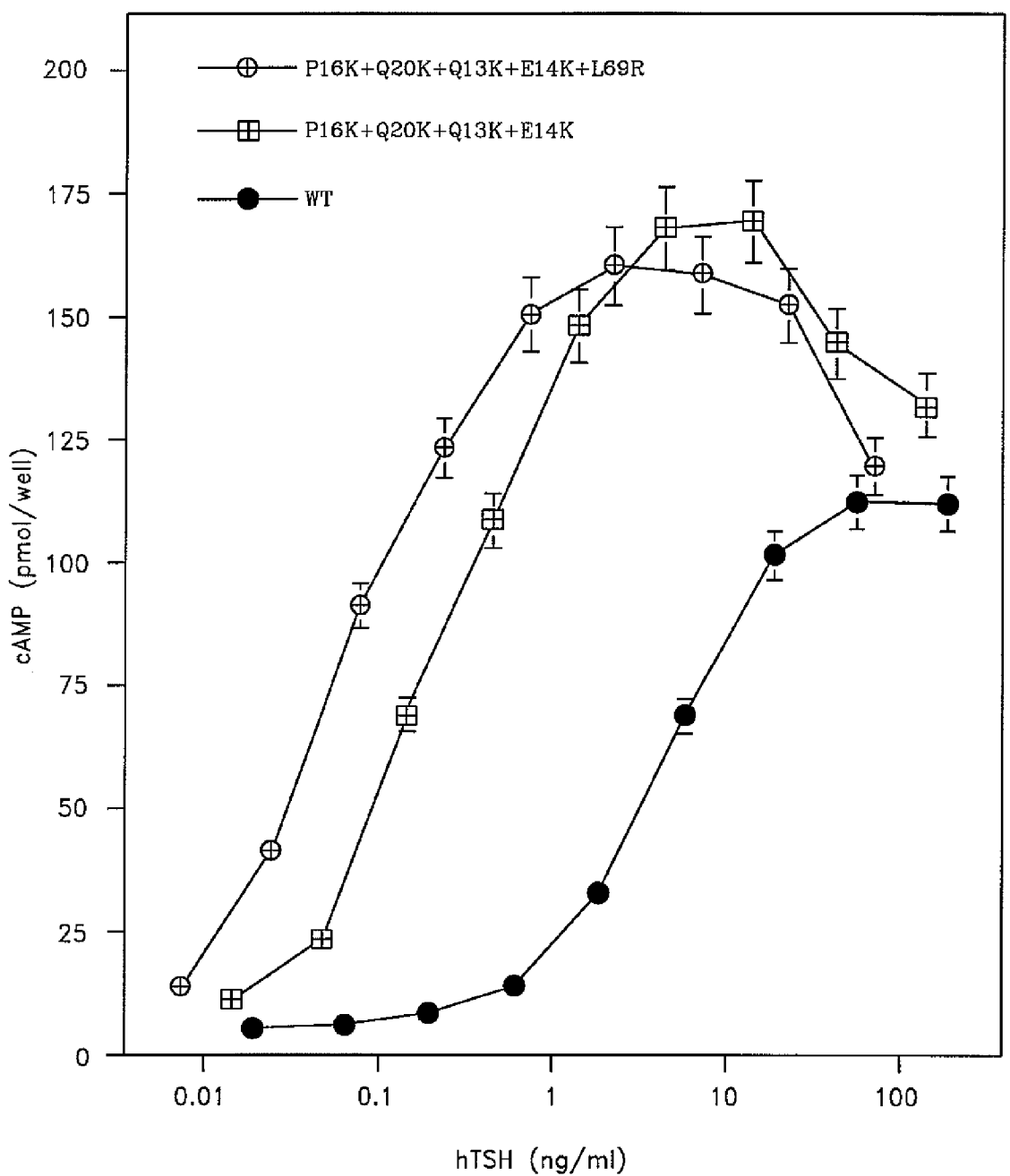
Figure 2C:
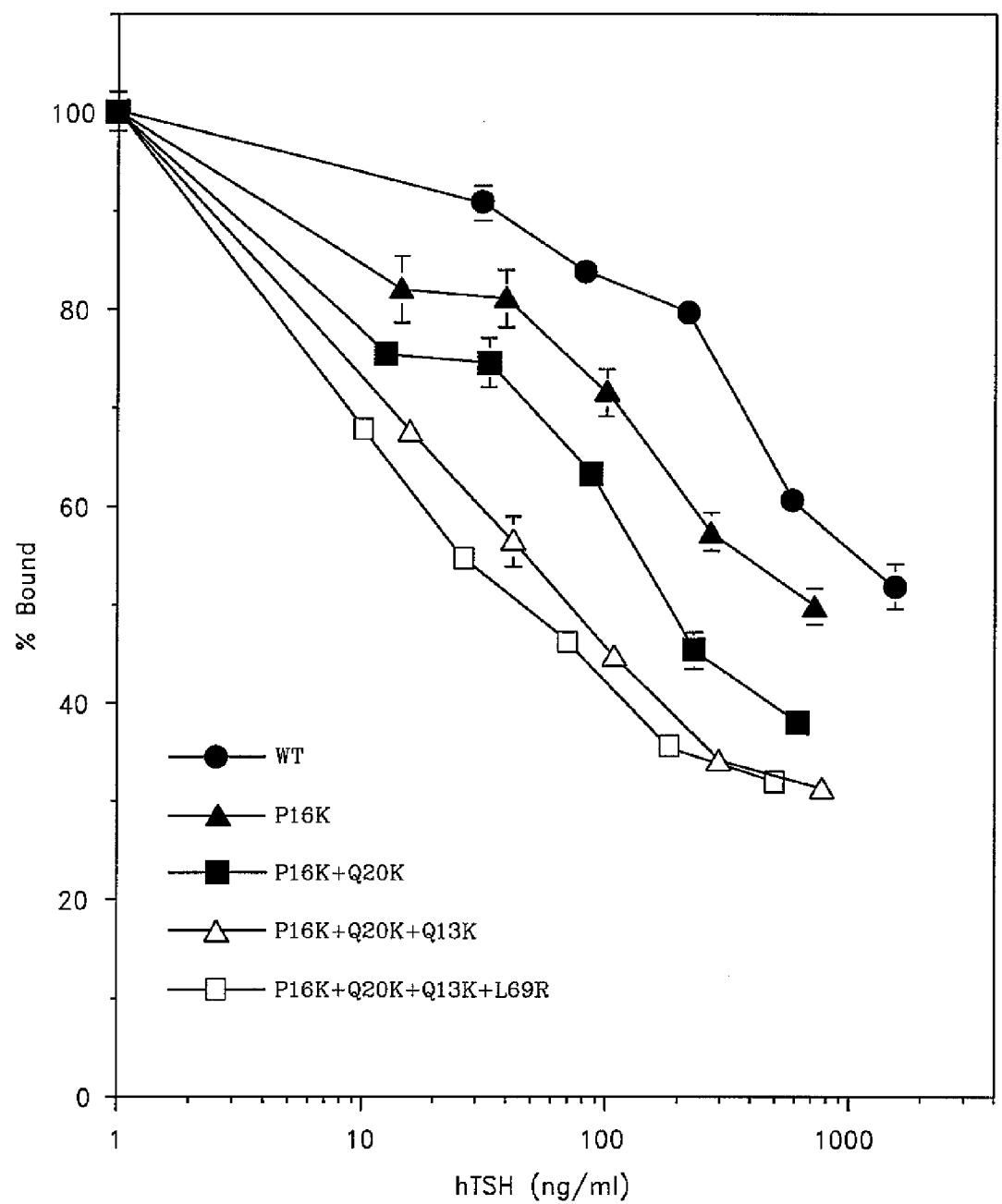
Figure 2D:
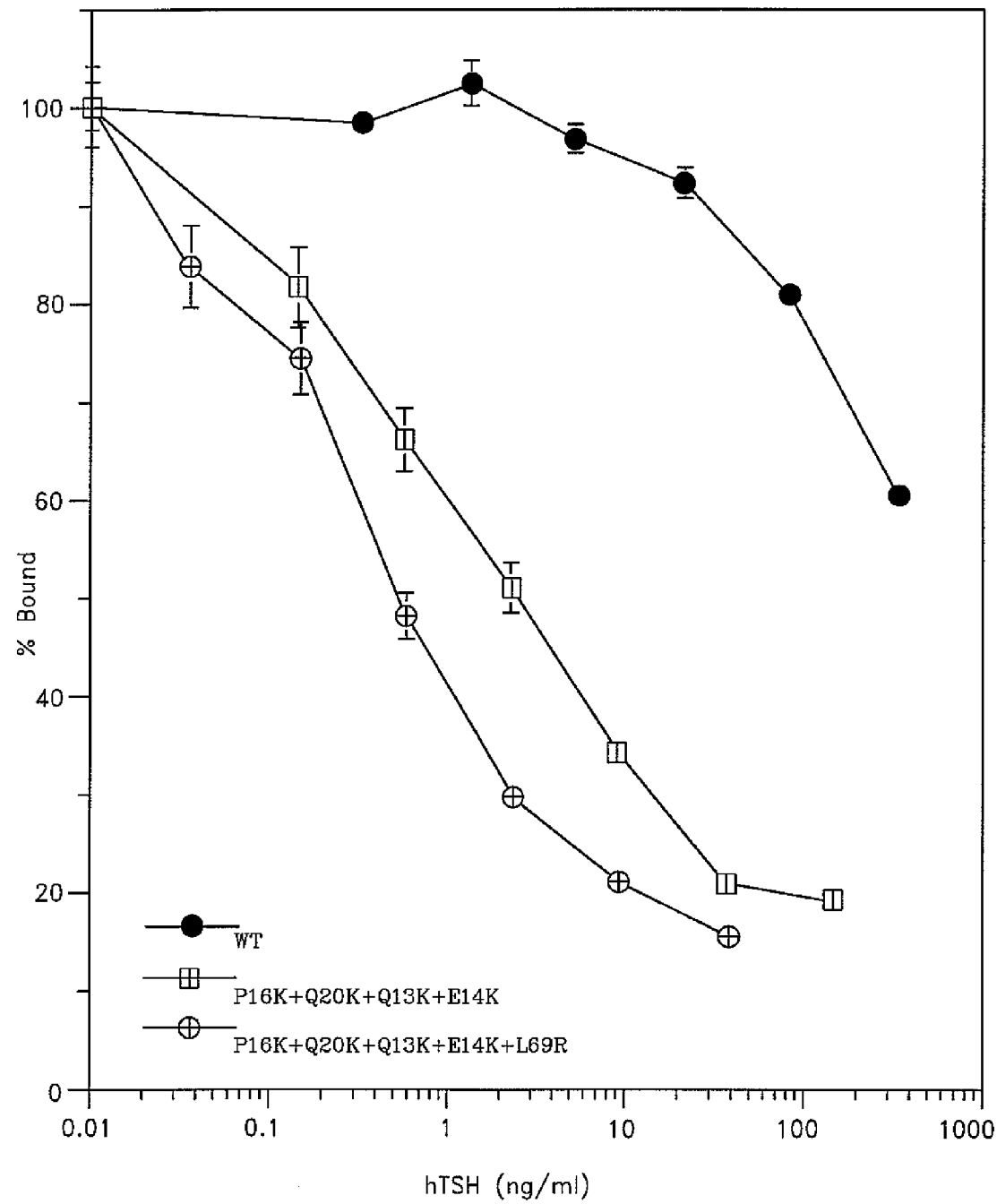
Figure 2E:
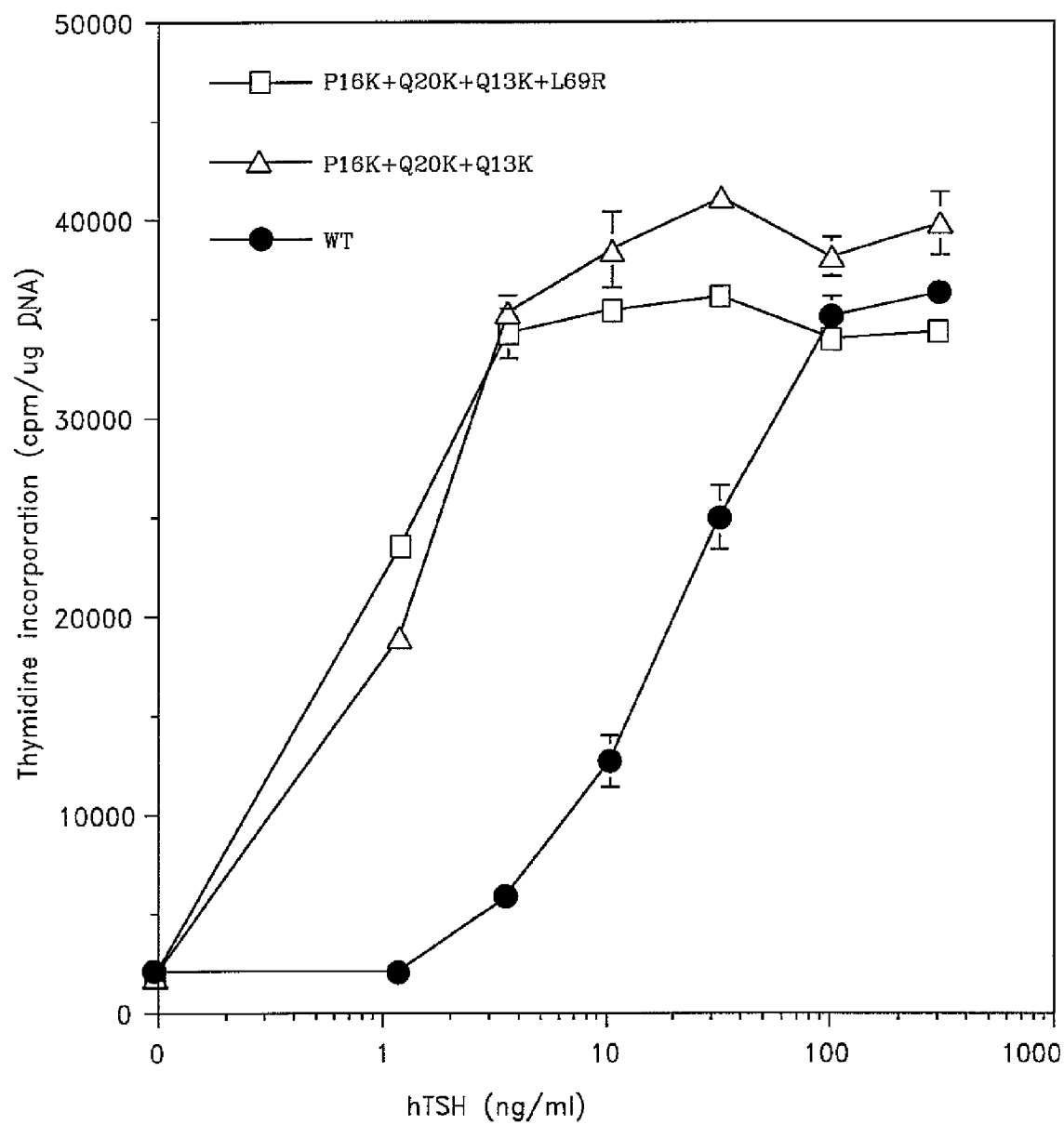
Figure 2F:
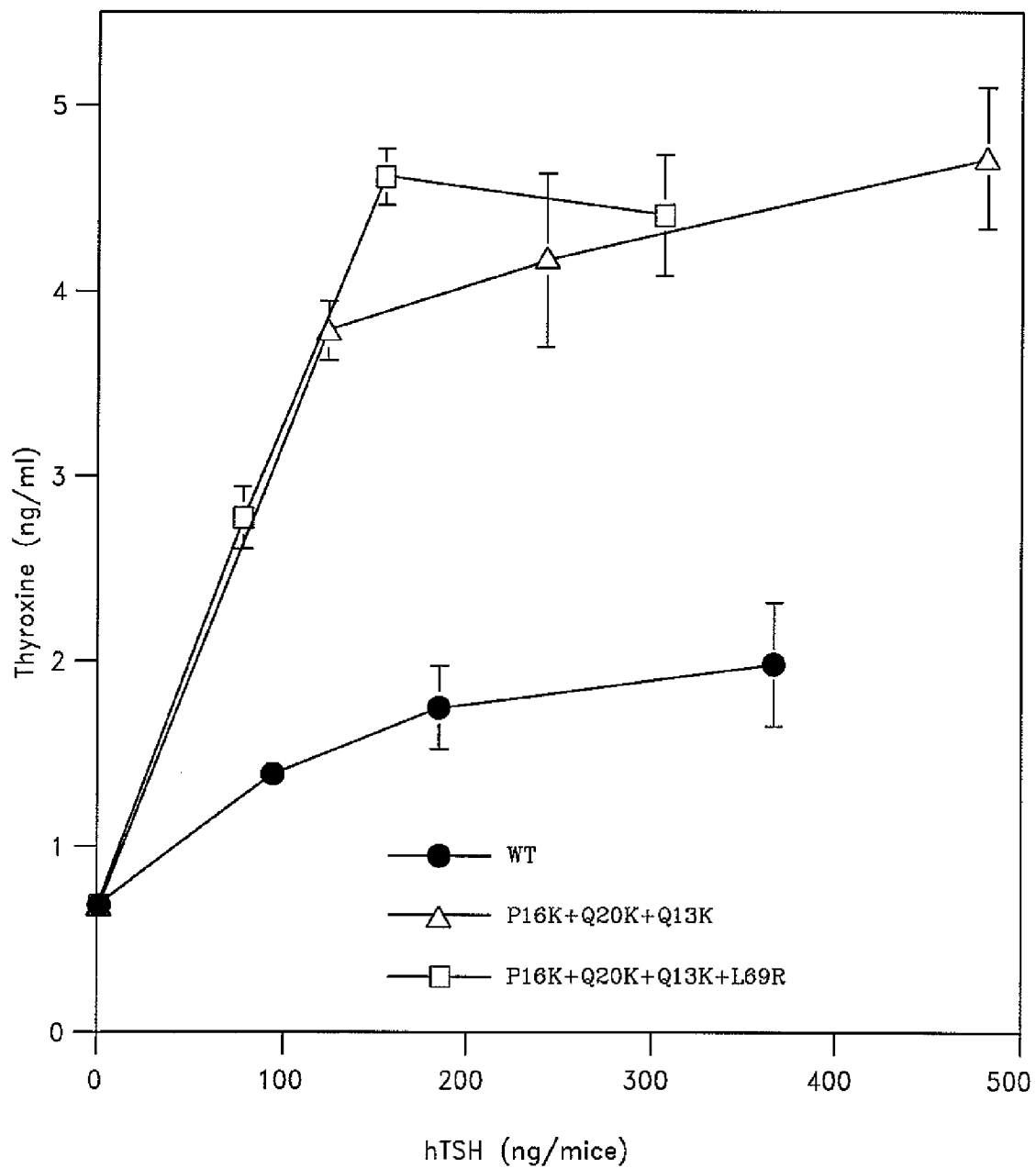

To further study the effect of Lys residues which were individually responsible for highest increases in potency, mutants containing multiple replacements were produced. The most active mutants are presented in FIGS. 2 and 3. The double Pro16→Lys+Gln20→Lys and the triple Pro16→Lys+Gln20→Lys+Gln13→Lys mutants showed, respectively, 12 and 24-fold higher activity than WT-hTSH, with a further increase in potency up to 35-fold after Leu69-Arg replacement in the TSHβ-subunit (FIG. 2a). Additional optimization included substitution Glu14-Lys (Lys in this position present in the tuna sequence) resulted in further increase in bioactivity up to 95-fold; these most potent multiple mutants elevated efficacy (maximal response) at least 1.5-fold (FIG. 2b). These increases were verified by testing the ability of hTSH mutants to bind to porcine as well as human TSH receptor (Table II, FIG. 2c and FIG. 2d), to induce growth in FRTL-5 cells (FIG. 2e), as well as $T_3$ production in cultured human thyroid follicles. In particular, Pro16→Lys+Gln20→Lys+Gln13→Lys/WT-hTSH-β and Pro16→Lys+Gln20→Lys+Gln13→Lys/Leu69→Arg mutants required, respectively, 18- and 27-fold lower concentration to attain half-maximal stimulation of ³H-thymidine incorporation in FRTL-5 cells than the WT-hTSH (FIG. 2e). The synergistic effect of multiple mutations on TSH bioactivity was not limited to a local cooperation of Lys residues in the 13-20 region of the α-subunit with receptor, but also involved the contribution of Arg69 in the opposite loop of β-subunit (Table II).

TABLE I

Relative expression of wild-type (WT) and mutant hormones in CHO-K1 cells

| | hTSH | hCG |
|---|---|---|
| WT | 100 ± 7 | 100 ± 4 |
| T11K | 267 ± 22 | 82 ± 2 |
| Q13K | 188 ± 9 | 106 ± 7 |
| P16K | 206 ± 25 | 72 ± 6 |
| Q20K | 149 ± 18 | 117 ± 8 |
| P16K + Q20K | 86 ± 9 | 62 ± 6 |
| Q13K + P16K + Q20K | 134 ± 6 | 76 ± 12 |
| Q13K + P16K + Q20K + E14K | 76 ± 12 | 52 ± 8 |
| P16K + F17T | 23 ± 10 | 93 ± 4 |
| Q50P | 174 ± 15 | 83 ± 3 |
| R67K | 171 ± 14 | 88 ± 6 |
| β-L69R | 74 ± 5 | n.a. |

TABLE I-continued

Relative expression of wild-type (WT)
and mutant hormones in CHO-K1 cells

|  | hTSH | hCG |
|---|---|---|
| Q13K + P16K + Q20K+ β-L69R | 86 ± 6 | n.a. |
| Q13K + P16K + Q20K + E14K + β-L69R | 25 ± 6 | n.a. | n.a. = not applicable.

Secretion levels are given as mean ± SEM relative to the WT, which was defined as 100% of WT-hTSH or WT-hCG respectively. The mean was calculated from at least four independent transfections, performed in at least five dishes for each mutant.

Figure 2G:
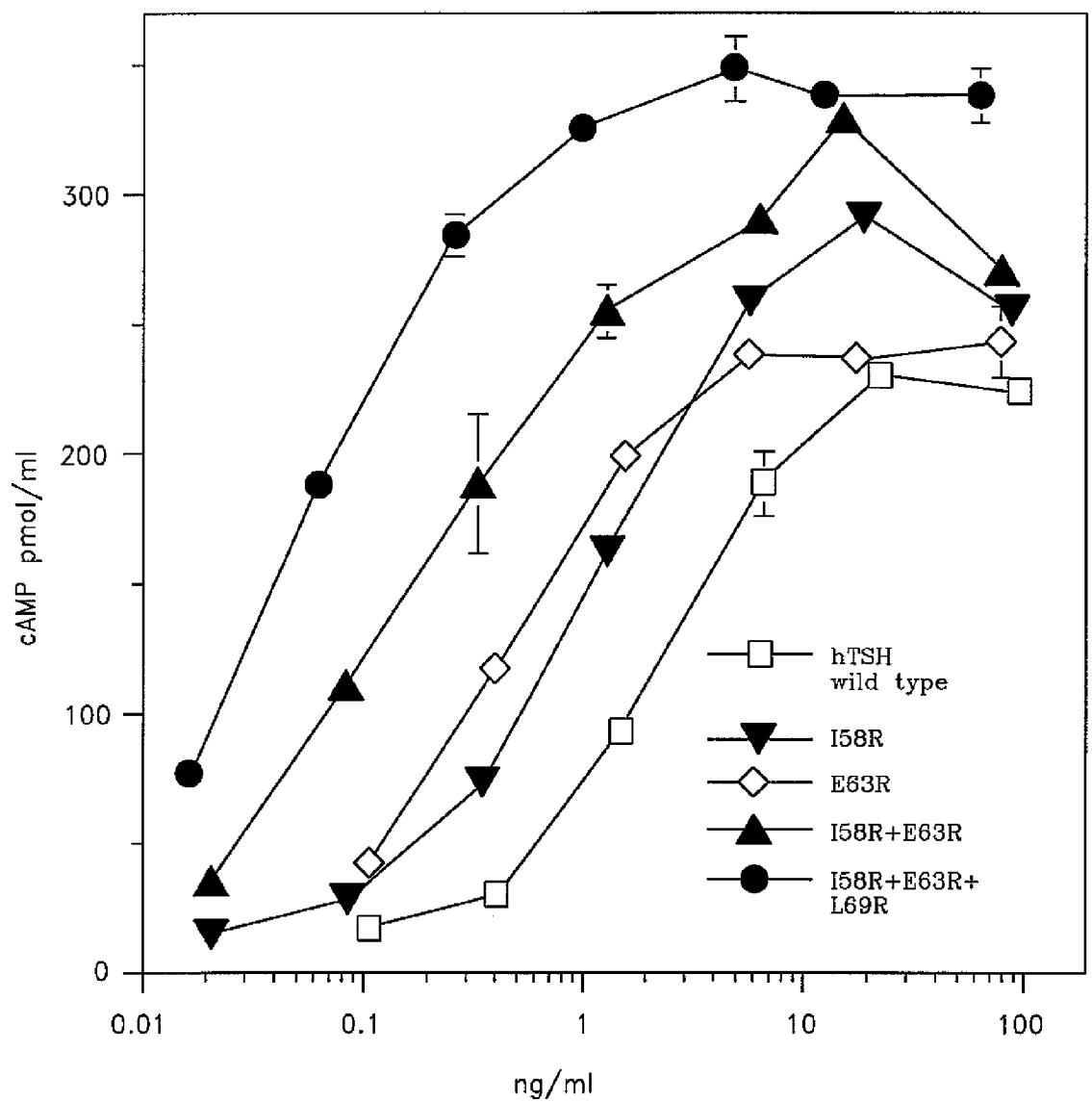
Figure 2H:
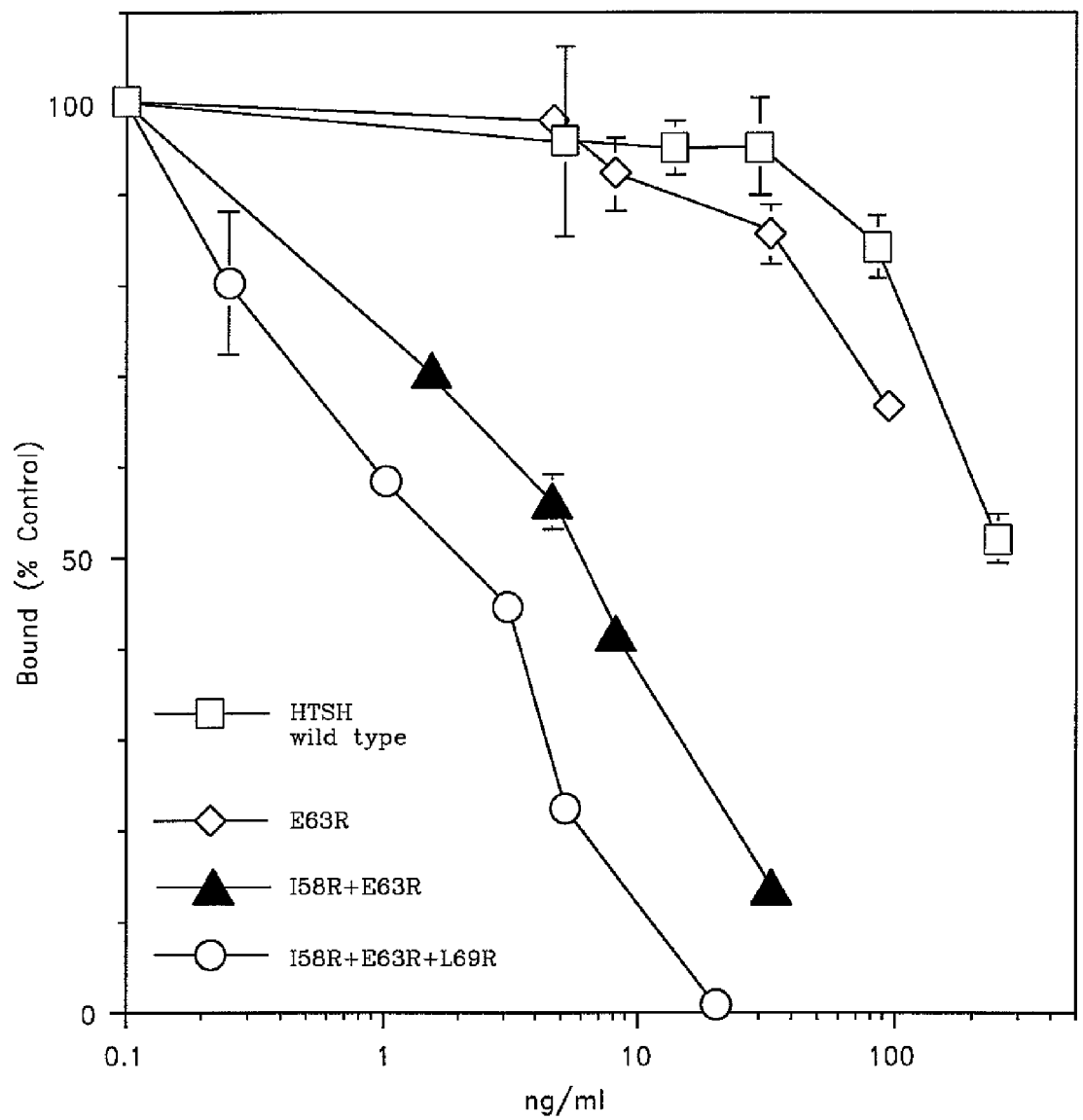
Figure 21:
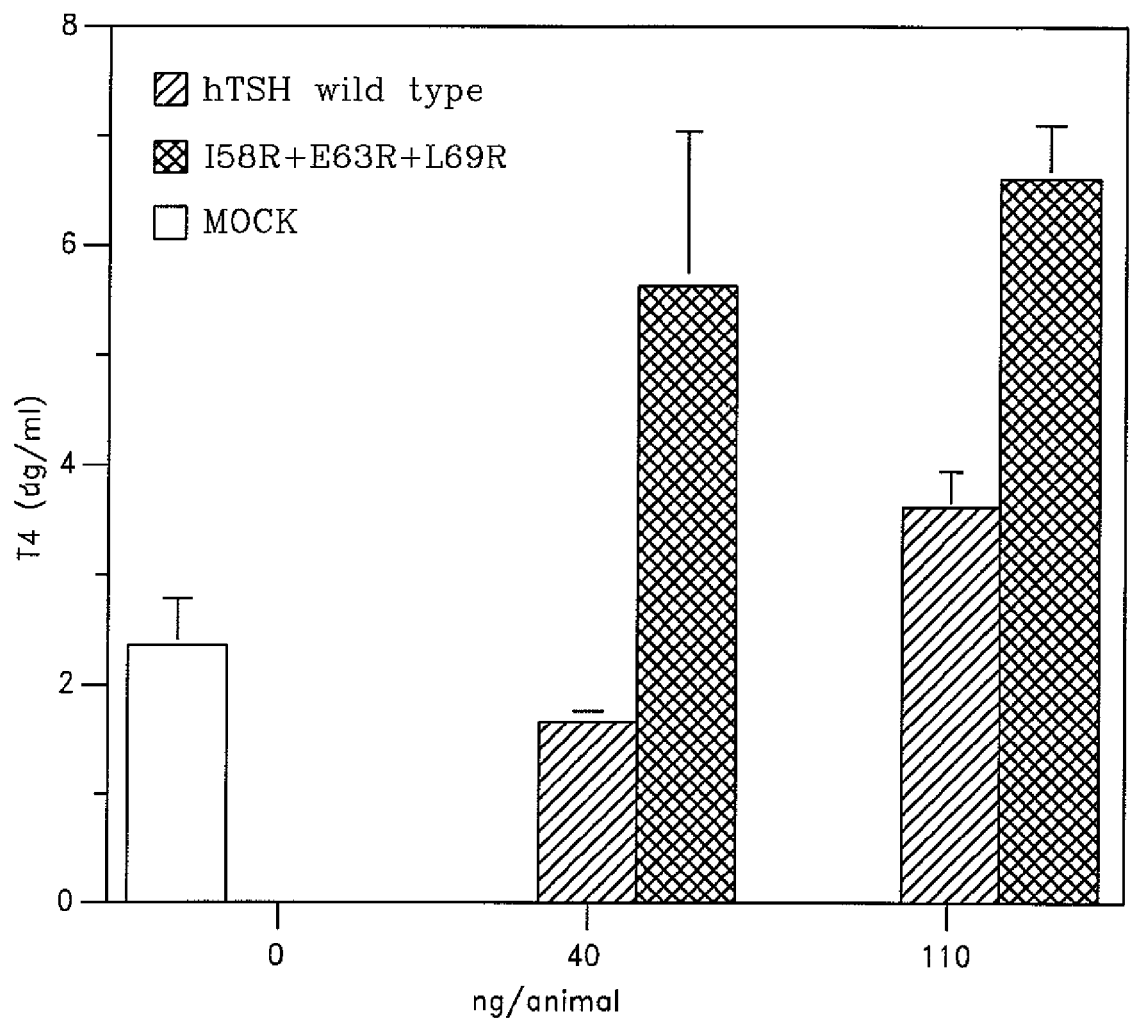

These findings were further confirmed in the animal model. A single injection of Pro16→Lys, Gln20→Lys and Gln13→Lys hTSH mutants in mice increased serum $T_4$ significantly higher than the WT-hTSH. Moreover, Pro16→Lys+Gln20→Lys+Gln13→Lys/WT-hTSHβ and Pro16→Lys+Gln20→Lys+Gln13→Lys/Leu69→Arg mutants also generated higher $T_4$ levels as compared to WT-hTSH (FIG. 2f). hTSH serum levels 6 h after i.p. injection in mice were similar and the hTSH analogs did not show compared to the WT great differences in the metabolic clearance rate.

combination of the two substitutions (I58R+E63R) resulted in the potency which was 15-fold higher than that of wild type hTSH and an 1.5-fold increase of efficacy (FIG. 2g). Potency and efficacy of the combination mutant I58R+E63R+L69R, in which three basic residues were introduced, was elevated 50-fold and 1.7-fold, respectively (FIG. 2g). These increases of intrinsic activity were accompanied by concomitant increases in receptor binding affinity, judged by a receptor-binding assay using CHO-JP09 cells. (FIG. 2h). Similarly, when mice were injected with the I58R+E63R+L69R mutant, their $T_4$ stimulation was significantly higher than in either mock or control treated mice. (FIG. 2i).

The bioactivity of hCG mutants was tested using progesterone stimulation in MA-10 cells and cAMP stimulation in COS-7 cells transfected with human LH/hCG receptor. hCG Lys mutants showed both higher potency (lower $EC_{50}$ values) as well as higher efficacy ($V_{max}$) than the WT-hCG (Table II, FIG. 3 a). The effect of single and multiple mutations was relatively analogous to that observed for the hTSH mutants. The αPro→16+Lys/WT-hCGP mutant was 4-fold more active than WT-hCG in the stimulation of progesterone production and receptor binding activity in MA-10 cells, with

TABLE II

The effects of site-specific mutagenesis of human glycoprotein hormones

| | hTSH | | | hTCG Progesterone synthesis in MA10 cells | |
|---|---|---|---|---|---|
| | cAMP stimulation in JP09 cells | | Inhibition of [125]I-bTSH | | |
| | EC50 (ng/ml) | Relative Potency (WT = 1) | binding EC25, ng/ml | EC50, ng/ml | Max, % |
| WT | 6.70 ± 0.69 | 1.0 | 81.3 ± 13.8 | 6.90 ± 1.04 | 100 ± 11 |
| T11K | 4.47 ± 0.79 | 1.5 | 68.3 ± 4.4 | 2.79 ± 0.25 | 156 ± 23 |
| Q13K | 1.89 ± 0.41 | 3.5 | 22.5 ± 2.6 | 2.46 ± 0.28 | 115 ± 24 |
| P16K | 1.05 ± 0.26 | 6.4 | 18.3 ± 3.6 | 2.05 ± 0.17 | 161 ± 31 |
| Q20K | 1.16 ± 0.22 | 5.8 | 21.3 ± 3.8 | 2.98 ± 0.27 | 134 ± 10 |
| P16K + Q20K | 0.57 ± 0.10 | 11.8 | 6.4 ± 2.4 | 1.70 ± 0.13 | 212 ± 34 |
| Q13K + P16K + Q20K | 0.28 ± 0.07 | 23.9 | 2.3 ± 0.3 | 1.58 ± 0.09 | 216 ± 36 |
| Q13K + P16K + Q20K + E14K | 0.17 ± 0.04 | 39.4 | 2.1 ± 0.4 | 1.65 ± 0.06 | 205 ± 41 |
| P16K + F17T | 3.52 ± 0.50 | 1.9 | n.d. | n.d. | n.d. |
| Q50P | 5.54 ± 0.70 | 1.2 | 77.5 ± 12.4 | 3.90 ± 0.85 | 137 ± 27 |
| R67K | 7.36 ± 0.33 | 0.9 | 62.5 ± 15.5 | 4.60 ± 0.63 | 145 ± 12 |
| TSHβ-L69R | 2.75 ± 0.49 | 2.4 | n.d. | n.a. | n.a. |
| TSHβ-L69R + Q13K + P16K + Q20K | 0.19 ± 0.06 | 35.3 | 1.8 ± 0.3 | n.a. | n.a. |
| TSHβ-L69R + Q13K + P16K + Q20K | 0.07 ± 0.02 | 95.7 | 1.3 ± 0.4 | n.a. | n.a. |
| bTSH | 0.71 ± 0.14 | 9.4 | 7.9 ± 2.5 | n.a. | n.a. | n.s.—no stimulation;
n.a.—not applicable;
n.d.—not determined.
A curve-fitting program, Mac Allfit (NIH, Bethesda, MD) was used to fit the dose-response data and calculate $EC_{50}$ and Vmax values.
Values are the mean ± SEM.
Pro16/Lys + Phe17/Thr mutant with glycosylation consensus sequence (Asn-Lys-Thr) was created to study the effect of neoglycosylation on hormone activity.

Figure 3A:
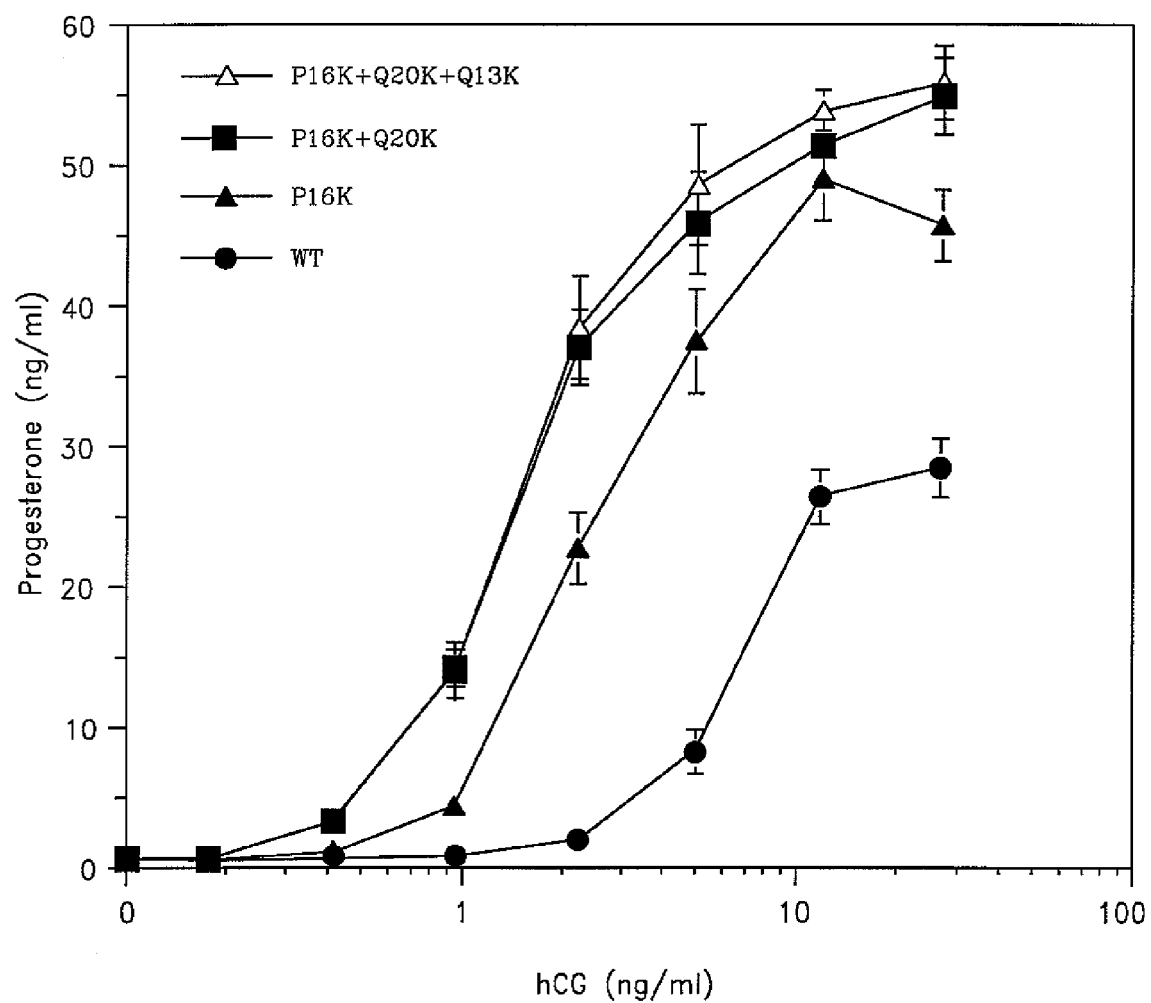
FIG. 3 shows the bioactivities and receptor binding activities of the most potent hCG analogs. Progesterone production stimulation (a) and receptor binding assay (b) in MA-10 cells. Data represent the mean±SEM of triplicate determinations from a representative experiment repeated three times. The relative maximal production levels of progesterone are presented in the Table II as % obtained with WT-hCG. cAMP stimulation (c) and receptor binding assay (d) in COS-7 cells expressing hLH receptor. Data represent the mean±SEM of triplicate determinations from a representative experiment repeated two times.
Figure 3B:
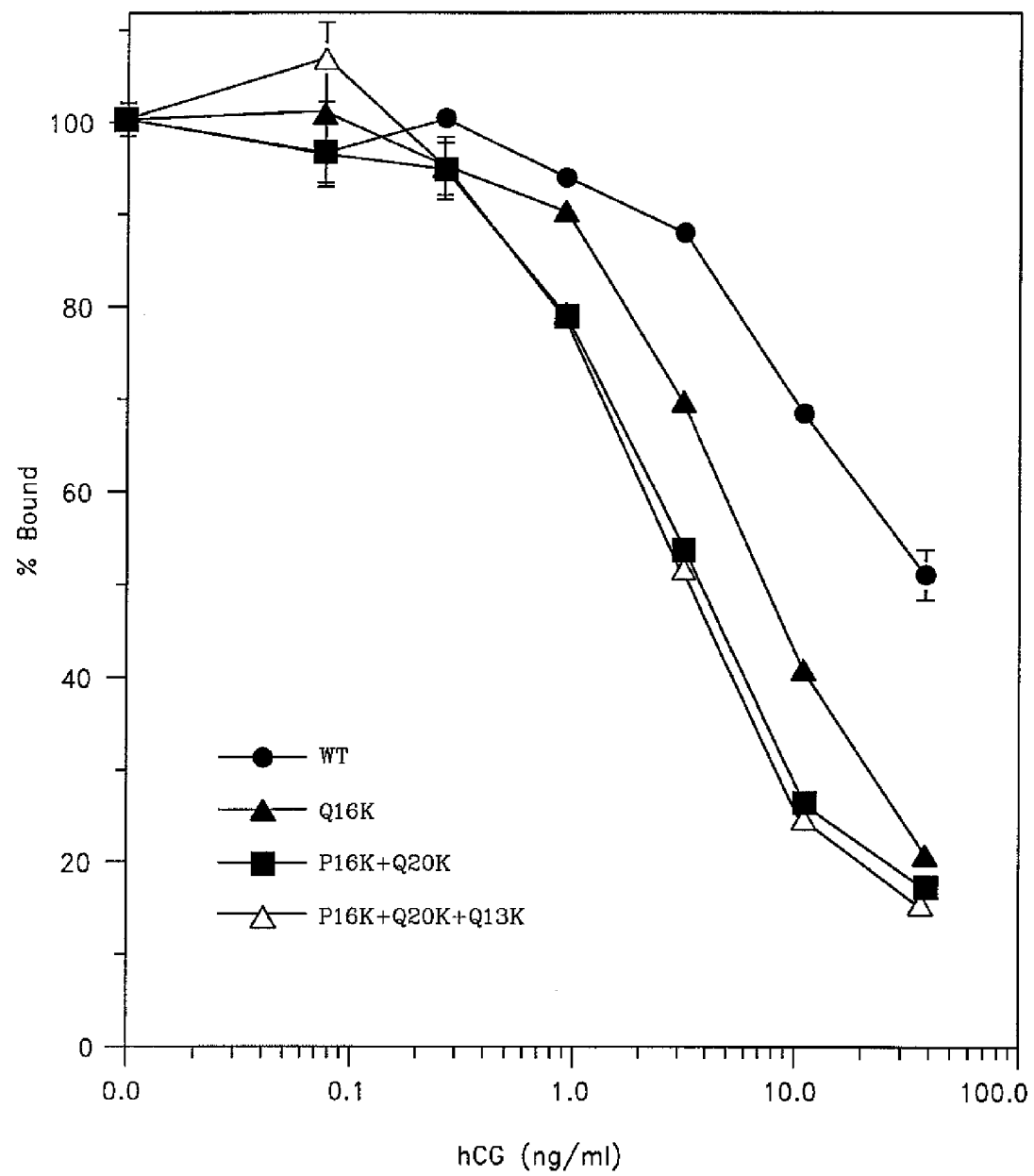
Figure 3C:
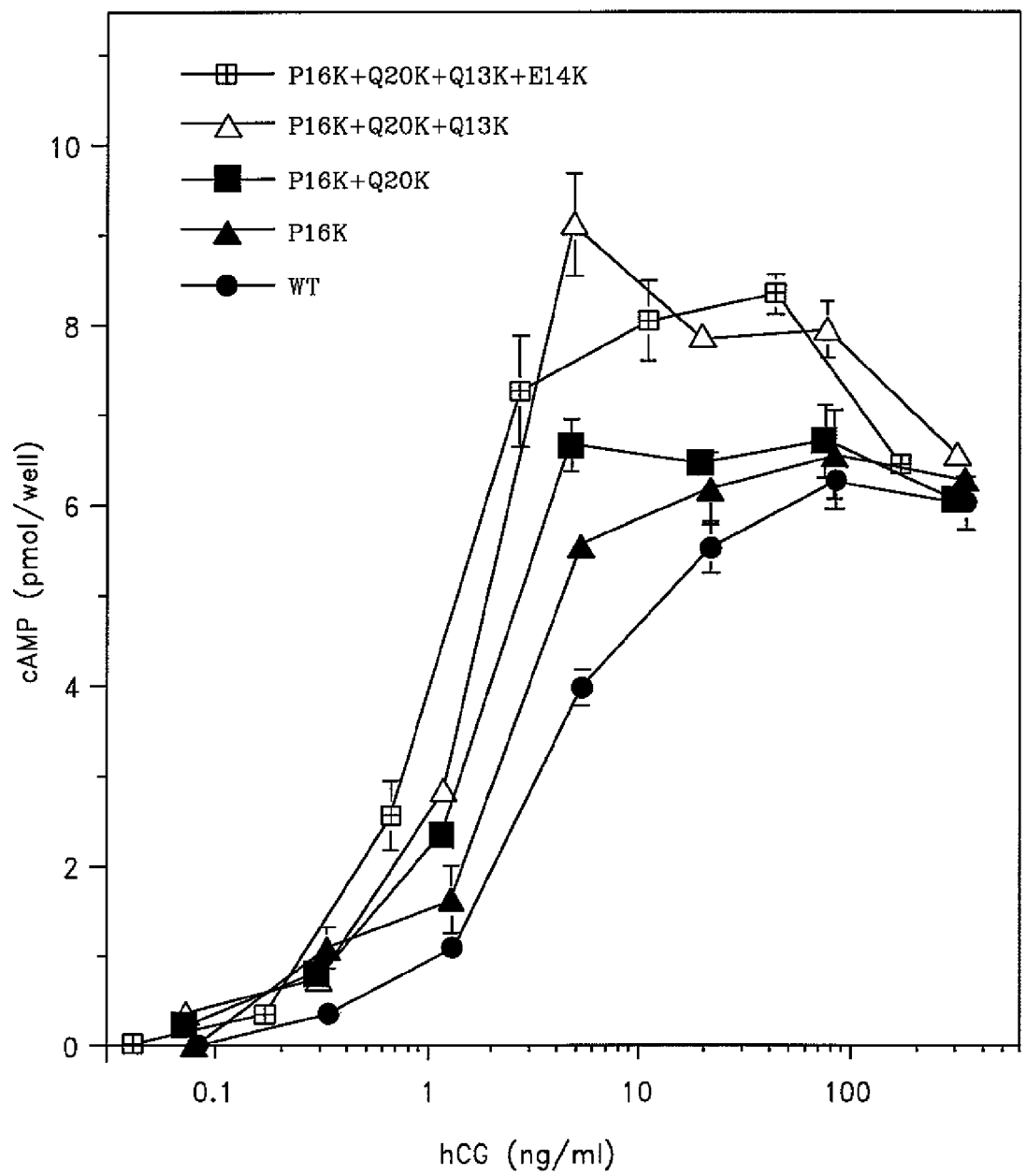
Figure 3D:
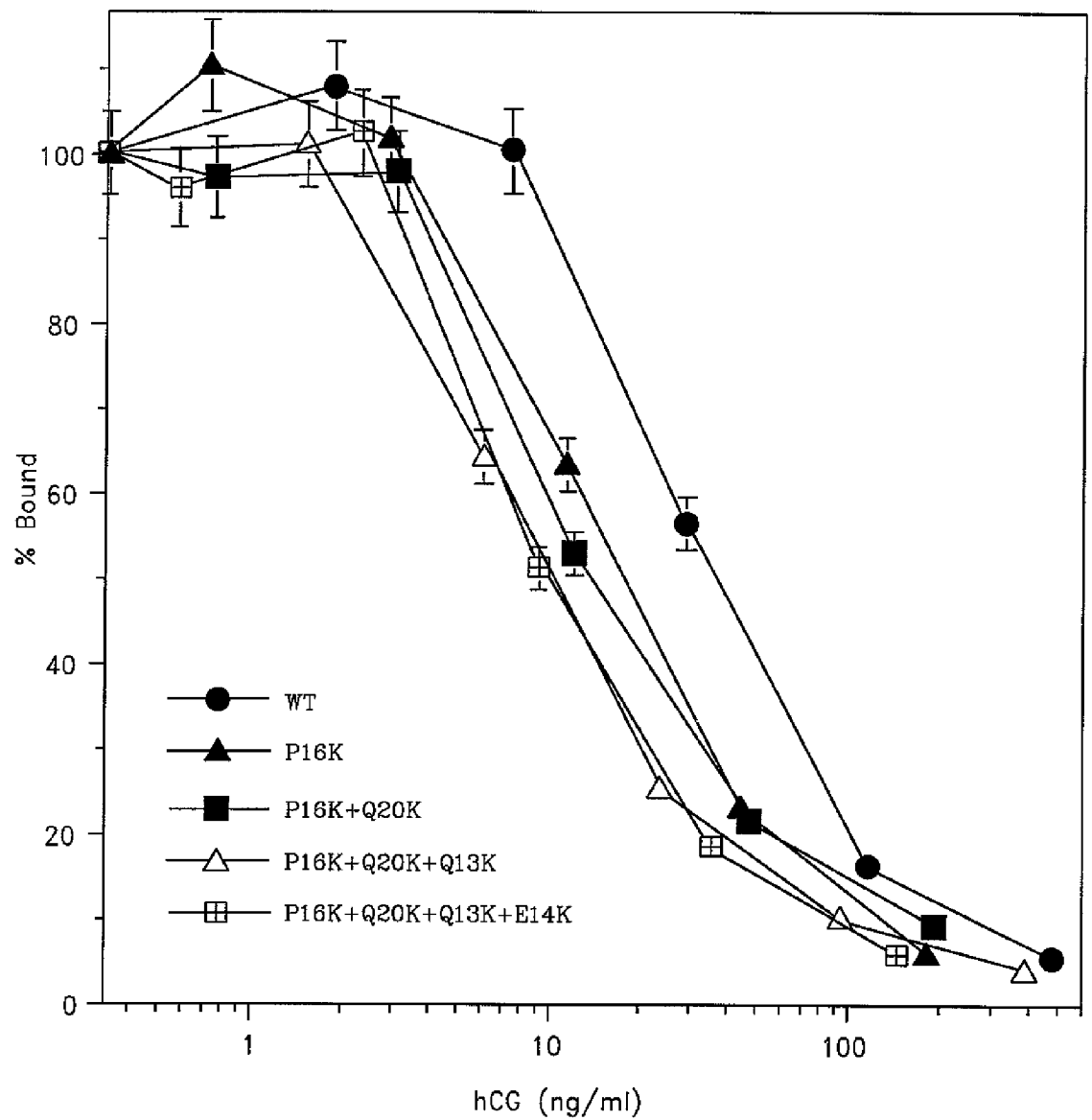

A sequence comparison of the hCG and hTSH β-subunits showed a region (residues 58-69 in TSHβ) which contains a cluster of basic residues in hCG, but not in hTSH. We used site-directed mutagenesis to introduce single and multiple basic residues into hTSH, based on their location in hCG, generating the additional hTSH β-subunit mutants: I58R, E63R, I58R+E63R, I58R+E63R+L69R. The mutant hTSH β-subunits were coexpressed with the human α-subunit and the intrinsic activity of the recombinant hTSH analogs studied at the rat THS receptor (FRTL-5 cells) and human TSH receptor (CHO-hTSHr cells). In both systems, single substitutions (I58R, E63R) increased potency of hTSH 2-fold to 4-fold, and led to a slight increase of efficacy (FIG. 2g). The further increases in both potency and efficacy for the Pro 16→Lys+Gln20→Lys and Pro 16-Lys+Gln20→Lys hCG+Gln13→Lys mutants (FIGS. 3a and 3b). Similar increases of intrinsic activity were also found when studied at the human LH/hCG receptor (COS-7-hLH/hCG-R cells) (FIGS. 3c and 3d).

Our data suggest that only a few amino acid replacements are sufficient to increase glycoprotein hormone bioactivity, even to a level higher than that of the model hormone (such as bTSH). Interestingly, only a few of the 40 differing residues between bovine and human TSH appear responsible for the higher biological activity of bTSH. The majority of the other replacements are conservative, and as illustrated by the R67K mutation in the α-subunit, seem to have no functional significance. In contrast, we show that surface-located Lys residues clustered in the L1 loop and β1-strand of the α-subunit are crucial for the high bioactivity of bTSH. Accordingly, recombinant hTSH with only two mutated amino acids (P16K+ Q20K) attains an intrinsic activity comparable to bTSH (Table II). Moreover, triple, quadruplicate and quintuple hTSH mutants show even higher potency than bTSH. These data suggest that the difference in activity between bTSH and hTSH is a result of several amino acid changes, including replacements increasing activity, but also others which may reduce biopotency of bTSH at the hTSH receptor.

Although, we cannot exclude a possibility that several receptor species would be made from a single transfected cDNA (by alternative splicing from cryptic sites or by post-translational modifications), the fact that similar differences in activity were observed in different cell systems argues strongly against the importance of different receptor species in the increase in potency, efficacy and affinity of these analogs. Furthermore, there is compelling evidence that naturally occurring hormone isoforms with various carbohydrate residues exert their effect at the post-receptor level with no or minimal effect on receptor binding affinity (Szkudlinski, M. W. et al. 1995 *Proc Natl Acad Sci USA* 92:9062-9066). Since the wild type hormones and their analogs were characterized in multiple experimental systems, it is highly probable that phenomenon of increased bioactivity described here is a rule rather than exception related to particular cell-dependent variant of the receptor.

Perspectives of Rational Design of Glycoprotein Hormone Analogs

Previous site-directed mutagenesis studies of glycoprotein hormones focused primarily on the highly conserved regions and residues, using such strategies as alanine scanning mutagenesis (Dias, et al. 1994 *J Biol Chem* 269:25289-25294) or multiple replacement approaches (Grossmann, M. et al. 1995 *Mol Endocrinol* 9:948-958). Several important studies were based on the creation of chimeric subunits using cassette mutagenesis and/or restriction fragment exchange (Lunardi-Iskandar, Y. et al. 1995 *Nature* 375:64-68; Campbell, R. K. et al. 1991 *Proc Natl Acad Sci* 88:760-764; Dias, J. A. et al. 1994 *J Biol Chem* 269:25289-25294). Our strategy based on replacement of nonconserved residues to those present in other species has been successful and permitted the generation of other glycoprotein hormone analogs, including hFSH mutants with increased bioactivity. The parallel improvement of bioactivity of hTSH, hCG and hFSH by introduction of basic residues in the 11-20 region of human α-subunit may be related to the fact that this region is distant from the β-subunit in the crystal structure based model of hCG and in our homology model of hTSH. The virtual identity of this area in both models as well as the observation that the antibodies binding to 11-26 region are not greatly influenced by subunit combination (Moyle, W. R. et al. 1995 *J Biol Chem* 270:20020-20031) suggest that this domain may function similarly in all the glycoprotein hormones. Once the α-subunit was successfully engineered to create more potent agonists of hTSH, hCG or hFSH, the same paradigm was used to modify their respective β-subunits to generate the ultimate superagonists of each glycoprotein hormone. For example, an additional replacement of a nonpolar Leu69 to Arg in the TSHβ-subunit resulted in further increase of hTSH bioactivity. In addition, the plasma half-life of our analogs can be modified regarding to specific therapeutic needs.

Further design and refinement of glycoprotein hormone analogs will include detailed three-dimensional structure of the hormone-receptor complexes. Although the exact structure of glycoprotein hormone receptors has not been solved, several models of hormone-receptor interaction have been proposed (Moyle, W. R. et al. 1995 *J Biol Chem* 270:20020-20031; Combarnous, Y. 1992 *Endocrine Rev* 13:670-691; Jiang, X. et al. 1995 *Structure* 3:1341-1353; Kajava, A. V. et al. 1995 *Structure* 3:867-877). In accordance with the recent model of Jiang et al. (Jiang, X. et al. 1995 *Structure* 3:1341-1353) the L1 loop of α-subunit may participate in the interaction with the transmembrane portion of the receptor. The cluster of positively charged residues in this loop may enhance such an interaction and facilitate further rearrangements in the receptor leading to the activation of G proteins and signal transduction.

Methods and Materials

Restriction enzymes, DNA markers and other molecular biological reagents were purchased from either Gibco BRL (Gaithersburg, Md.) or from Boehringer-Mannheim (Indianapolis, Ind.). Cell culture media, fetal bovine serum and LipofectAMINE were purchased from Gibco BRL (Gaithersburg, Md.). VentR DNA Polymerase was purchased from New England Biolabs (Beverly, Mass.). The full length human α cDNA (840 bp) subcloned into BamHI/XhoI sites of the pcDNA I/Neo vector (Invitrogen Corp., San Diego, Calif.) and hCG-β gene were obtained from Dr. T. H. Ji (University of Wyoming, Laramie, Wash.). The hTSH-β minigene without the first intron, with the non-translated 1st exon and authentic translation initiation site was constructed in our laboratory. rhTSH-G standard was from Genzyme Corp. (Framingham, Mass.). The CHO cells with stably expressed hTSH receptor (CHO-hTSHR clone JP09 and clone JP26) were provided by Dr. G. Vassart (University of Brussels, Brussels, Belgium). The human LH receptor cDNA was obtained from Dr. T. Minegishi (Gunma University, Gunma, Japan). FRTL-5 cells were kindly supplied by Dr. L. D. Kohn (NIDDK, NIH, Bethesda, Md.). MA-10 cells were generously supplied by Dr. M. Ascoli (University of Iowa, Iowa City, Iowa). $^{125}$I cAMP and $^{125}$I-hTSH were from Hazleton Biologicals (Vienna, Va.). Blood samples of various primates were obtained from Yerkes Regional Primate Research Center (Emory University, Atlanta, Ga.) and Animal Resources (University of Oklahoma, Oklahoma City, Okla.).

Determination of Primate α-Subunit Sequences

The QIAamp® Blood Kit (Qiagen Inc., Chatsworth, Calif.) was used for extraction of genomic DNA from whole blood samples of chimpanzee (*Pan troglodytes*), orangutan (*Pongo pygmaeus*), gibbon (*Hylobates* sp.) and baboon (*Papio anubis*). Genomic DNA was used in the PCR; the synthetic oligonucleotide primers used were:

```
                                        (SEQ ID NO: 1)
5'-CCTGATAGATTGCCCAGAATGC-3' (sense)
and (SEQ ID NO: 2)
5'-GTGATAATAACAAGTACTGCAGTG-3' (antisense),
``` and were synthesized according to the nucleotide sequence of the gene encoding common α-subunit of human glycoprotein hormones (Fiddes, J. C. and Goodman, H. M. 1979 *Nature* 281:351-356). PCR was performed using 800-1000 ng of genomic DNA template and 10 picomoles of each primer in 100 μl reaction volume that also contained 10 mM Tris-HCl, (pH 9.0 at 25° C.), 50 mM KCl, 2.5 mM MgCl$_2$, 200 μM dNTPs and 2 U of Taq DNA Polymerase (Promega Corp. Madison, Wis.). The reaction mix was covered with mineral oil, and each sample was initially heated to 95° C. for 10 min. The PCR program consisted of 32 cycles of denaturation at 95° C. for 1 min 30 sec, annealing at 55° C. for 1 min 30 sec and extension at 72° C. for 1 min, followed by a final extension period at 72° C. for 7 min. The reactions were then directly electrophoresed on a 1% agarose gel in the presence of ethidium bromide. The amplified PCR product (~700 bp), spanning the nucleotide sequence of exon 3, intron 3 and exon 4, was purified using QIAquick PCR Purification Kit (QIAGEN Inc., Chatsworth, Calif.) and subcloned into pCR™II using Original TA Cloning Kit (Invitrogen Corp., San Diego, Calif.). The sequence of the fragment was obtained after subcloning or direct dideoxy sequencing using a Sequenase kit (U.S. Biochemical Corp., Cleveland, Ohio).

Homology Modeling

Modeling relies on the strong sequence homology between hCG and hTSH. The sequences were aligned to bring the cysteine-knot residues into correspondence and the percentage of identical as well as highly conservative replacements were calculated as described (Wu, H. et al. 1994 *Structure* 2:545-558). There was 58% sequence identity between hCG and hTSH molecules; 31% of the two β-subunit sequences were identical and additional 17% included highly conservative changes in β-subunit. A molecular model of hTSH was built on a template of hCG model derived from crystallographic coordinates obtained from the Brookhaven Data Bank (Lapthorn, A. J. et al. 1994 *Nature* 369:455-461). All coordinate manipulations and energy calculations were done using CHARMm release 21.2 for the Convex and further modified using the molecular graphic package QUANTA (Version 3.3, Molecular Simulations Inc., University of York, York, United Kingdom).

Site-Directed Mutagenesis

Mutagenesis of the human. α-cDNA and the hTSHβ minigene was accomplished by the PCR-based megaprimer method (Sarkar, G. and Sommer, S. S. 1990*BioTechniques* 8:404-407). Amplification was optimized using Vent® DNA Polymerase (New England Biolabs, Beverly, Mass.). After digestion with BamHI and XhoI PCR product was ligated into pcDNA I/Neo (Invitrogen Corp., San Diego, Calif.) with the BamI/XhoI fragment excised. MC1061/p3 *E. coli* cells were transformed using Ultracomp *E. coli* Transformation Kit (Invitrogen Corp.). The QIAprep 8 Plasmid Kit (QIAGEN Inc., Chatsworth, Calif.) was used for multiple plasmid DNA preparations. QIAGEN Mega and Maxi Purification Protocols were used to purify larger quantities of plasmid DNA. Multiple mutants were created with the same method using plasmids containing α-cDNA with a single mutation as a template for further mutagenesis. Mutations were confirmed by double stranded sequencing using Sanger's dideoxynucleotide chain termination procedure.

Expression of Recombinant Hormones

CHO-K1 Cells (ATCC, Rockville, Md.) were maintained in Ham's F-12 medium with glutamine and 10% FBS, penicillin (50 units/ml) and streptomycin (50 µg/ml). Plates of cells (100 mm culture dishes) were cotransfected with wild type or mutant α-cDNA in the pcDNAI/NEO and hTSHβ minigene inserted into the p(LB)CMV vector (Joshi, L. et al. 1995 *Endocrinology* 136:3839-3848), or pcDNAI/Neo containing hCGP-cDNA (Ji, I., 1993 *Biol Chem* 268:22971-22974) using a LipofectAMINE (Gibco BRL, Gaithersburg, Md.). After 24 h, the transfected cells were transferred to CHO-serum free medium (CHO—SFM-II, Gibco BRL,). The culture media including control medium from mock transfections using the expression plasmids without gene inserts were harvested 72 h after transfection, concentrated and centrifuged; the aliquots were stored at −20° C. and thawed only once before each assay. WT and mutant hTSH were measured and verified using four different immunoassays as described (Grossmann, M. et al. 1995 *Mol Endocrinol* 9:948-958). Concentrations of WT and mutant hCG were measured using chemiluminescence assay (hCG Kit, Nichols Institute, San Juan Capistrano, Calif.) and immunoradiometric assay (hCG IRMA, ICN, Costa Mesa, Calif.).

cAMP Stimulation in JP09 Cells Expressing Human TSH Receptor

CHO cells stably transfected with hTSH receptor cDNA (JP09) were grown and incubated with serial dilutions of WT and mutant hTSH as described (Grossmann, M. et al. 1995 *Mol Endocrinol* 9:948-958). cAMP released into the medium was measured by radioimmunoassay (Szkudlinski, M. W. et al. 1993 *Endocrinology* 133:1490-1503). The equivalent amounts of total media protein were used as the mock control and the hTSH containing samples from transfected cells.

cAMP Stimulation in COS-7 Cells Expressing Human LH Receptor

COS-7 cells transiently transfected with hLH receptor cDNA were grown and incubated with serial dilutions of WT and mutant hCG essentially as described (Igarashi, S. et al. 1994 *Biochem Biophys Res Commun* 201:248-256). cAMP released into the medium was measured by radioimmunoassay (Szkudlinski, M. W. et al. 1993 *Endocrinology* 133:1490-1503). The equivalent amounts of total media protein were used as the mock control and the hCG containing samples from transfected cells.

Progesterone Production Stimulation in MA-10 Cells

Transformed murine Leydig cells (MA-10) grown in 96-well culture plates were incubated with WT and mutant hCG for 6 hours in the assay medium as described (Ascoli, M. 1981 *Endocrinology* 108:88-95). The amount of progesterone released into the medium was determined by radioimmunoassay (CT Progesterone Kit, ICN Biomedicals, Inc., Costa Mesa, Calif.).

Receptor Binding Assays

The receptor-binding activities of hTSH analogs were assayed by their ability to displace $^{125}$I-bTSH from a solubilized porcine thyroid membranes[224]. The binding activities of selected analogs to human TSH receptor was tested using JP09 cells. The binding activities of hCG analogs to MA-cells and to COS-7 cells transiently transfected with human LH receptor were determined using $^{125}$I-hCG and assay medium as described previously (Ascoli, M. 1981 *Endocrinology* 108: 88-95).

Thymidine Uptake Stimulation in FRTL-5 Cells

Growth of the rat thyroid cells (FRTL-5) was monitored as previously described (Szkudlinski, M. W. et al. 1993 *Endocrinology* 133:1490-1503).

Stimulation of $T_4$ Secretion in Mice

The in vivo bioactivity of the WT and mutant TSH was determined using a modified McKenzie bioassay (Szkudlinski, M. W. et al. 1993 *Endocrinology* 133:1490-1503; Moyle, W. R. et al. 1994 *Nature* 268:251-255). WT and mutant TSH were injected i.p. into male albino Swiss Cr1:CF-1 mice with previously suppressed endogenous TSH by administration of 3 µg/ml $T_3$ in drinking water for 6 days. Blood samples were collected 6 h later from orbital sinus and the serum $T_4$ and TSH levels were measured by respective chemiluminescence assays (Nichols Institute).

It will be apparent to those skilled in the art that various modifications and variations can be made in the present invention without departing from the scope or spirit of the invention Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A modified human luteinizing hormone (LH) comprising an α subunit and a β subunit, said α subunit comprising at least three basic amino acids at positions selected from the group consisting of positions 11, 13, 14, 16, 17, and 20.

2. The modified LH of claim 1, wherein said α subunit further comprises a fourth basic amino acid at a position selected from the group consisting of positions 11, 13, 14, 16, 17, and 20.

3. The modified LH of claim 2, wherein said basic amino acids in the α subunit are at positions 11, 13, 16, and 20.

4. The modified LH of claim 2, wherein said basic amino acids in the α subunit are at positions 11, 13, 17, and 20.

5. The modified LH of claim 2, wherein said basic amino acids in the α subunit are at positions 13, 14, 16, and 20.

6. The modified LH of claim 2, wherein said basic amino acids in the α subunit are at positions 13, 14, 17, and 20.

7. The modified LH of claim 2, said α subunit further comprising a fifth basic amino acid at a position selected from the group consisting of positions 11, 13, 14, 16, 17, and 20.

8. The modified LH of claim 7, wherein said basic amino acids in the α subunit are at positions 13, 14, 16, 17, and 20.

9. The modified LH of claim 7, wherein said basic amino acids in the α subunit are at positions 11, 13, 14, 16 and 20.

10. The modified LH of claim 1, wherein said basic amino acids in the α subunit are at positions 11, 13, 14, 16, 17, and 20.

11. The modified LH of claim 1, wherein said basic amino acids in the α subunit are at positions 13, 16, and 20.

12. The modified LH of claim 1, wherein the basic amino acids are lysine.

13. The modified LH of claim 1, wherein the basic amino acids are selected from the group consisting of lysine and arginine.

14. A nucleic acid encoding the modified LH of claim 1.

15. A vector comprising the nucleic acid of claim 14, wherein the vector is suitable for expressing the nucleic acid.

16. A host comprising the vector of claim 15, wherein the host is suitable for expressing the nucleic acid.

17. The modified LH of claim 1 further modified so that the modified LH has less than five amino acid substitutions in the α-subunit in positions other than positions 11, 13, 14, 16, 17, and 20.

18. The modified LH of claim 1, wherein the modified LH has less than four amino acid substitutions in the α-subunit in positions other than positions 11, 13, 14, 16, 17, and 20.

19. The modified glycoprotein hormone of claim 1, wherein the modified LH has less than three amino acid substitutions in the α-subunit in positions other than positions 11, 13, 14, 16, 17, and 20.

20. The modified LH of claim 1, wherein the modified LH has less than two amino acid substitutions in the α-subunit in positions other than positions 11, 13, 14, 16, 17, and 20.

21. The modified LH of claim 1, wherein the modified LH has complete amino acid sequence homology with human LH in positions other than positions 11, 13, 14, 16, 17, and 20 of the α-subunit.

22. A modified human luteinizing hormone (LH) comprising a basic amino acid in the α-subunit in at least one position selected from the group consisting of positions 11, 13, 14, 16, 17 and 20.

23. The modified LH of claim 22, wherein a basic amino acid is at position 11.

24. The modified LH of claim 22, wherein a basic amino acid is at position 13.

25. The modified LH of claim 22, wherein a basic amino acid is at position 14.

26. The modified LH of claim 22, wherein a basic amino acid is at position 16.

27. The modified LH of claim 22, wherein a basic amino acid is at position 17.

28. The modified LH of claim 22, wherein a basic amino acid is at position 20.

29. The modified LH of claim 22, wherein the basic amino acid is selected from the group consisting of lysine and arginine.

30. The modified LH of claim 22, comprising a basic amino acid in at least two positions selected from the group consisting of positions 11, 13, 14, 16, 17, and 20.

31. The modified LH of claim 30, wherein the basic amino acids are at positions 16 and 20.

32. The modified LH of claim 30, wherein the basic amino acids are at positions 16 and 13.

33. The modified LH of claim 30, wherein the basic amino acids are at positions 20 and 13.

34. The modified LH of claim 30, wherein the basic amino acid is selected from the group consisting of lysine and arginine.

35. A nucleic acid encoding the modified LH of claim 22.

36. A vector comprising the nucleic acid of claim 22, wherein the vector is suitable for expressing the nucleic acid.

37. A host comprising the vector of claim 36, wherein the host is suitable for expressing the nucleic acid.

38. The modified LH of claim 22 further modified so that the modified LH has less than five amino acid substitutions in the α-subunit in positions other than positions 11, 13, 14, 16, 17, and 20.

39. The modified LH of claim 22, wherein the modified-LH has less than four amino acid substitutions in the α-subunit in positions other than positions 11, 13, 14, 16, 17, and 20.

40. The modified LH of claim 22, wherein the modified-LH has less than three amino acid substitutions in the α-subunit in positions other than positions 11, 13, 14, 16, 17, and 20.

41. The modified LH of claim 22, wherein the modified LH has less than two amino acid substitutions in the α-subunit in positions other than positions 11, 13, 14, 16, 17, and 20.

42. The modified LH of claim 22, wherein the modified LH has the complete amino acid sequence homology with the wild-type LH in positions other than positions 11, 13, 14, 16, 17, and 20 of the α-subunit.

* * * * *

UNITED STATES PATENT AND TRADEMARK OFFICE
CERTIFICATE OF CORRECTION

| | | |
|---|---|---|
| PATENT NO. | : 8,044,187 B2 | |
| APPLICATION NO. | : 12/467081 | |
| DATED | : October 25, 2011 | |
| INVENTOR(S) | : Mariusz W. Szkudlinski, Bruce D. Weintraub and Mathis Grossmann | |

It is certified that error appears in the above-identified patent and that said Letters Patent is hereby corrected as shown below:

At column 1, line 17 of the specification, immediately following the "Related Applications" paragraph and immediately preceding the "Sequence Listing" paragraph, please insert the following heading and paragraph which was errantly omitted:

--STATEMENT REGARDING FEDERALLY SPONSORED RESEARCH OR DEVELOPMENT
The instant application was made with government support; the government has certain rights in this invention.--

Signed and Sealed this
Twenty-ninth Day of May, 2012

David J. Kappos
*Director of the United States Patent and Trademark Office*